(12) United States Patent
Guillon et al.

(10) Patent No.: US 8,506,539 B2
(45) Date of Patent: Aug. 13, 2013

(54) EYELID MARGIN WIPES COMPRISING CHEMICAL MEANS FOR TEMPERATURE ADJUSTMENT

(75) Inventors: Michel Guillon, London (GB); Cecile Adrienne Maissa, London (GB)

(73) Assignee: Optometric Technology Group LTD., London (GB)

( * ) Notice: Subject to any disclaimer, the term of this patent is extended or adjusted under 35 U.S.C. 154(b) by 954 days.

(21) Appl. No.: 11/120,757

(22) Filed: May 3, 2005

(65) Prior Publication Data

US 2006/0018953 A1  Jan. 26, 2006

Related U.S. Application Data

(63) Continuation of application No. PCT/GB03/04782, filed on Nov. 5, 2003.

(30) Foreign Application Priority Data

Nov. 5, 2002  (GB) .................................. 0225795.4

(51) Int. Cl.
  *A61F 7/03*  (2006.01)
  *A61M 35/00*  (2006.01)
(52) U.S. Cl.
  USPC ......................................... 604/294; 604/291
(58) Field of Classification Search
  USPC .......................... 604/289, 291, 294; 606/162
  See application file for complete search history.

(56) References Cited

U.S. PATENT DOCUMENTS

| | | | | |
|---|---|---|---|---|
| 3,472,242 | A | * | 10/1969 | Demner ........................ 132/333 |
| 3,977,202 | A | | 8/1976 | Cross et al. |
| 4,749,080 | A | * | 6/1988 | Toohey ........................ 206/210 |
| 4,883,454 | A | * | 11/1989 | Hamburg ......................... 604/1 |
| 4,913,682 | A | * | 4/1990 | Shabo ............................. 604/1 |
| 5,447,981 | A | * | 9/1995 | Fock et al. .................... 524/458 |
| 5,662,624 | A | | 9/1997 | Sundstrom et al. |
| 6,090,060 | A | | 7/2000 | Radow et al. |
| 6,265,631 | B1 | | 7/2001 | Angelillo et al. |
| 6,287,580 | B1 | * | 9/2001 | Gott et al. .................... 424/401 |
| 6,409,746 | B1 | | 6/2002 | Igaki et al. |
| 6,465,709 | B1 | | 10/2002 | Sun et al. |
| 2002/0020407 | A1 | * | 2/2002 | Wohland et al. ......... 126/263.03 |
| 2002/0103520 | A1 | | 8/2002 | Latham |
| 2002/0192267 | A1 | * | 12/2002 | Smadi et al. .................. 424/443 |
| 2004/0063603 | A1 | * | 4/2004 | Dave et al. .................... 510/438 |

FOREIGN PATENT DOCUMENTS

| | | | |
|---|---|---|---|
| CA | 2346223 A1 | * | 8/2001 |
| CA | 2505138 C | | 6/2012 |
| EP | 1 090 614 A | | 4/2001 |
| EP | 1587468 B1 | | 1/2011 |
| GB | 2394898 B | | 3/2007 |
| JP | 62-183786 A | | 11/1987 |
| JP | 63-77590 A | | 5/1988 |
| JP | 06-007395 | | 1/1994 |
| JP | 08-133966 | | 5/1996 |
| JP | 11-33076 A | | 2/1999 |
| JP | 2000005209 A | * | 1/2000 |
| JP | 2001-245915 | | 9/2001 |
| JP | 2002-078727 | | 3/2002 |
| JP | 5101796 A | | 12/2012 |
| WO | WO 98/29079 | | 7/1998 |
| WO | WO 01/03619 | | 7/2000 |
| WO | WO 0126499 A1 | * | 4/2001 |
| WO | WO 0128382 A1 | * | 4/2001 |

OTHER PUBLICATIONS

Definition of impregnated, Oxford English Dictionary, http://www.oed.com/, accessed online on Mar. 3, 2011.*
JPO machine translation of JP 2002-078727 A, http://dossier1.ipdl.inpit.go.jp/, accessed online on Mar. 14, 2013.*
JPO machine translation of JP 2000-005209 A, http://dossier1.ipdl.inpit.go.jp/, accessed online on Mar. 14, 2013.*
Gutgésell, et al. *Histopathology of Meibomian Gland Dysfunction*, Journal of Ophthalmology vol., 94, 383-387 (1982).
Hom, et al., *Prevalence of Meibomian Gland Dysfunction*, Optometry & vision Science, vol. 67, No. 9 pp. 710-712.
Ong, et al, *Relation Between Contact Lens Wear and Meibomian Gland Dysfunction*, Optometry & Vision Science, vol. 7, No. 3 pp. 208-210.
Anonymous, *Blepharitis, Stye and Chalazion*, Online www.eye-net.gr/english/public/blepharitis.html.
Materials Safety Data Sheet, Ferrous Oxide, Powder Technology Inc., Nov. 14, 2007.
Gutgesell, et al. *Histopathology of Meibomian Gland Dysfunction*, Journal of Ophthalmology vol., 94, 383-387 (1982).
Hom, et al., *Prevalence of Meibomian Gland Dysfunction*, Optometry & vision Science, vol. 67, No. 9 pp. 710-712, Pub year 1990.
Ong, et al., *Meibomian Gland Dysfunction: Some Clinical, Biochemical and Physical Observations*, Ophthal. Physio. Opt. (1990) vol. 10 pp. 144-148.
Ong, et al, *Relation Between Contact Lens Wear and Meibomian Gland Dysfunction*, Optometry & Vision Science, vol. 7, No. 3 pp. 208-210, Pub year 1996.
Tiffany, et al., *The Influence of Composition on Physical Properties of Meibomian Secretion*, Dry Eye Institute, (1986) pp. 597-608.
Anonymous, *Blepharitis, Stye and Chalazion*, Online www.eye-net.gr/english/public/blepharitis.html, Pub year 2000.
International Search report for PCT application No. PCT/GB2003/04782, mailed on Apr. 16, 2004.

* cited by examiner

*Primary Examiner* — Shaojia Anna Jiang
*Assistant Examiner* — Jonathan S Lau
(74) *Attorney, Agent, or Firm* — Wilson Sonsini Goodrich & Rosati

(57) ABSTRACT

An eyelid margin wipe comprising chemical means for adjusting the temperature of the wipe relative to the ambient temperature. The wipe is particularly useful for treatment of disorders of the eyelid or eyelid margin such as meibomian gland dysfunction.

31 Claims, 22 Drawing Sheets

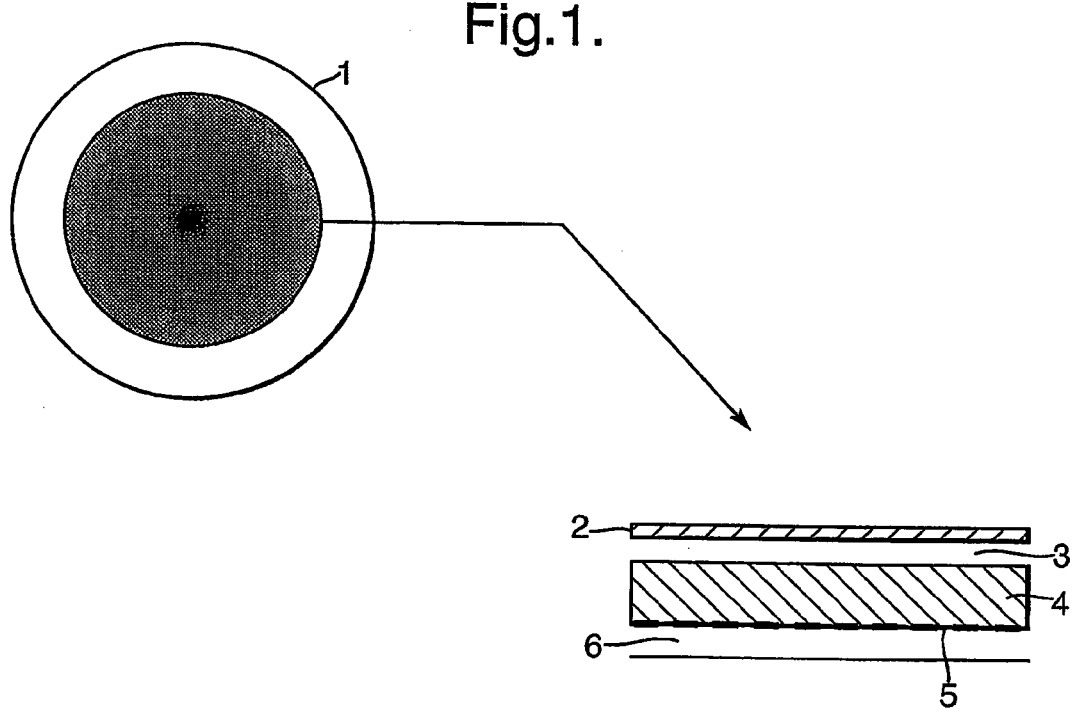

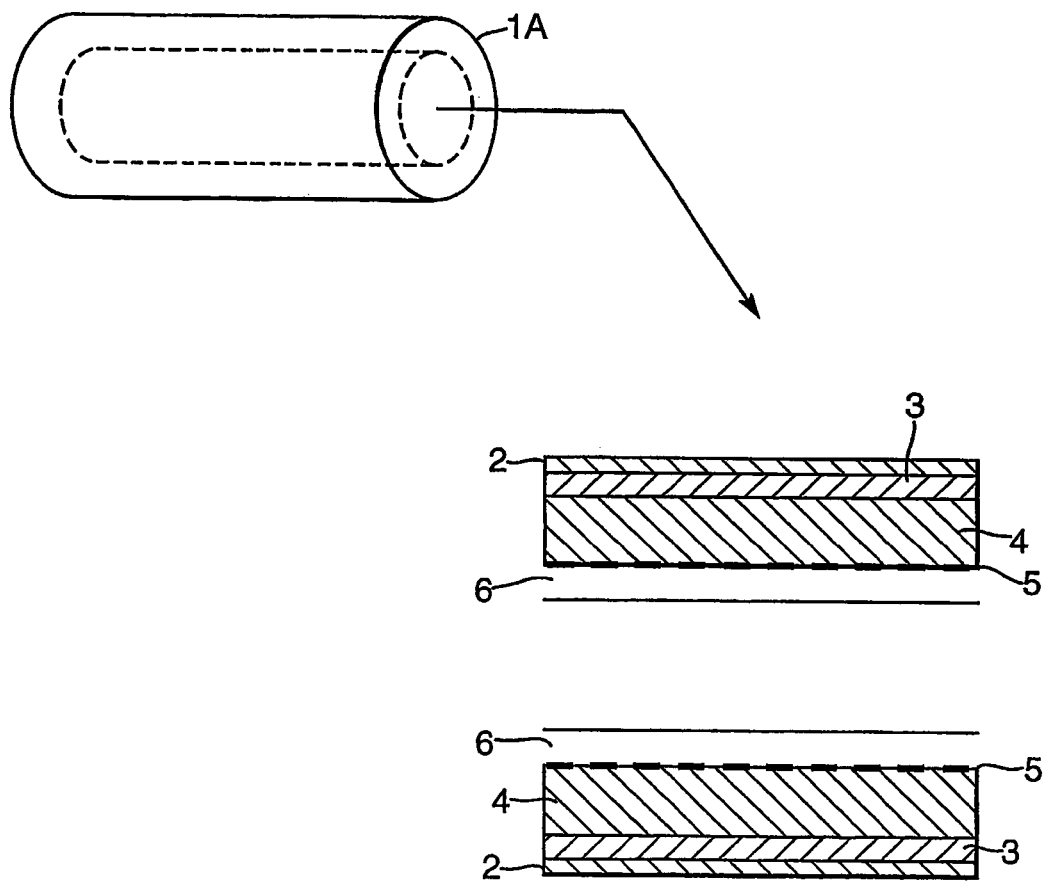

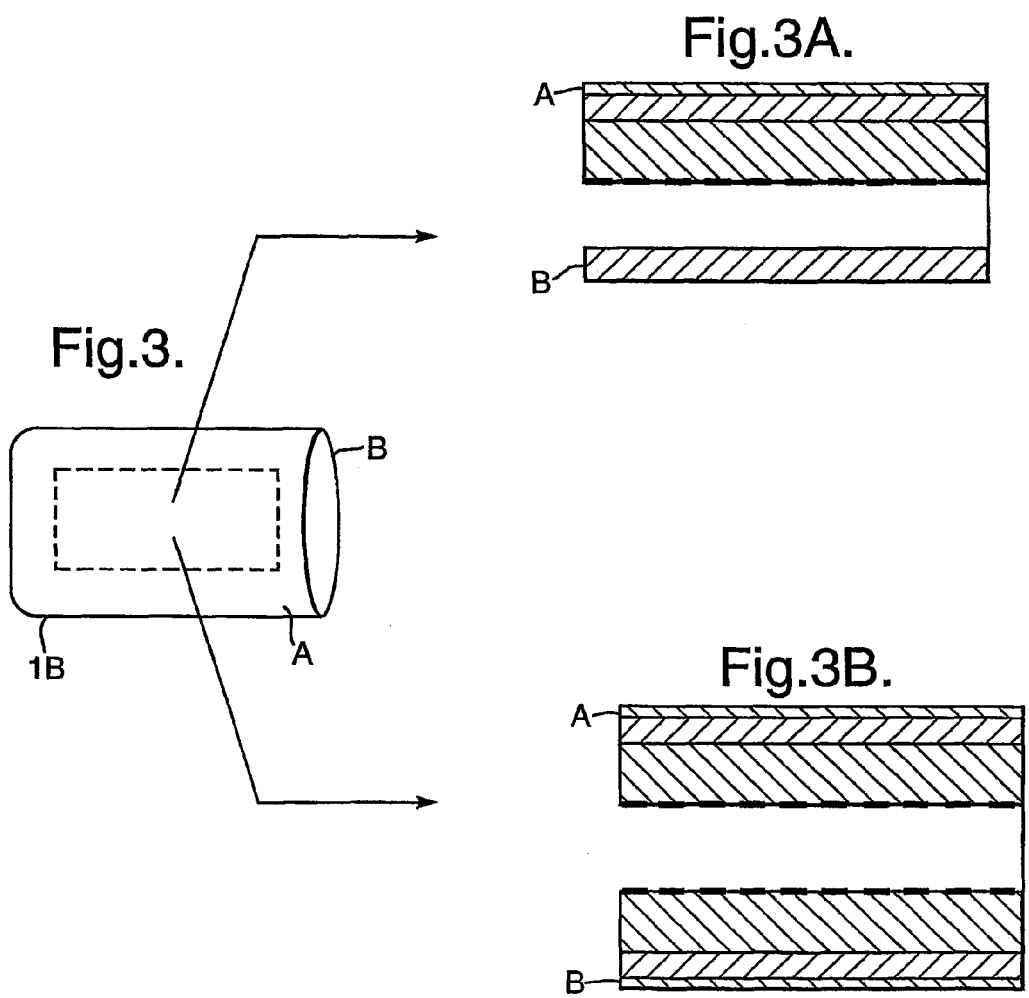

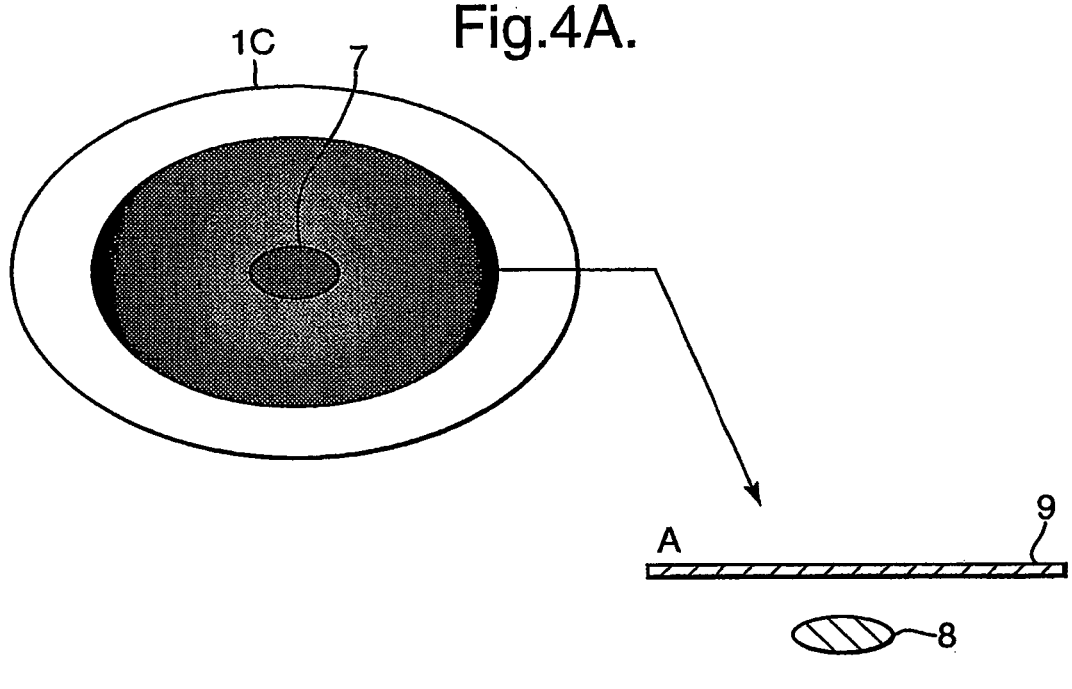
Fig.4A.
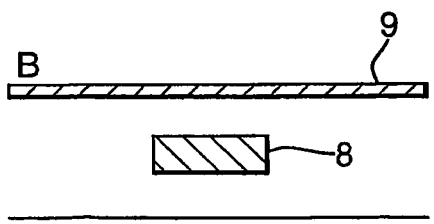

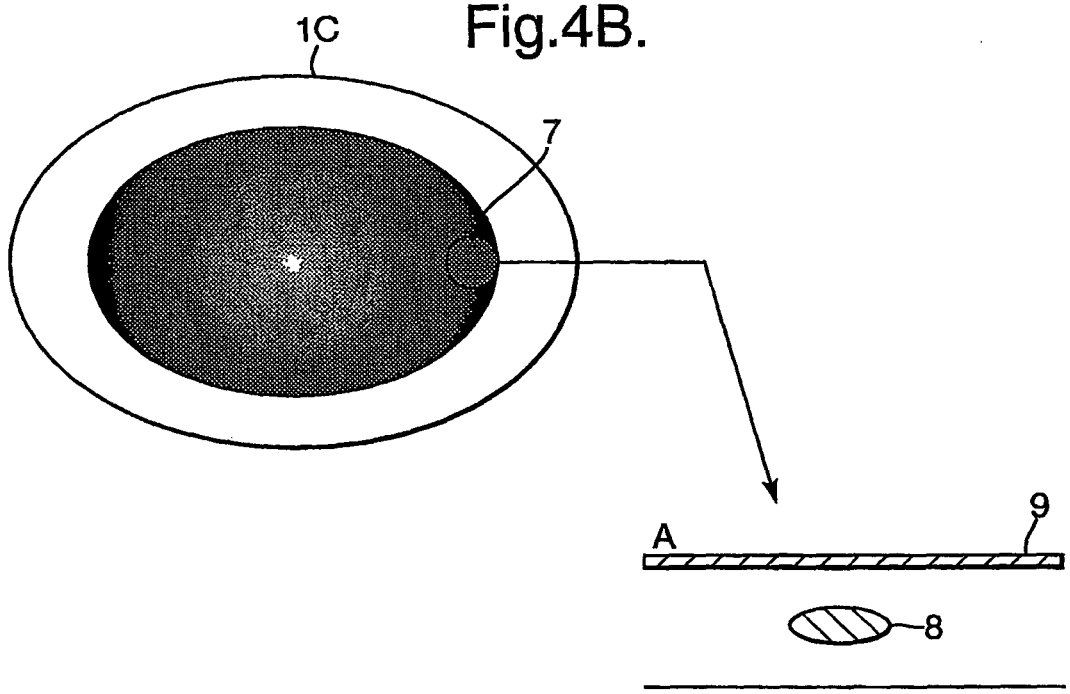
Fig.4B.
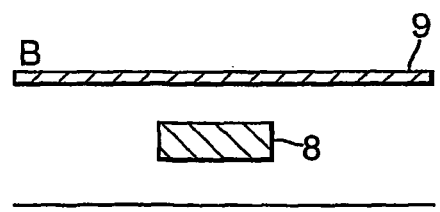

Fig.5.
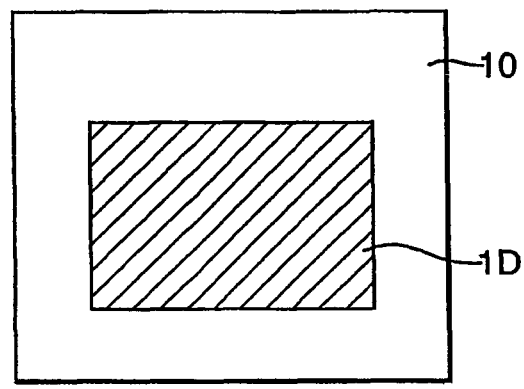
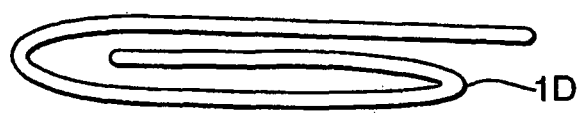
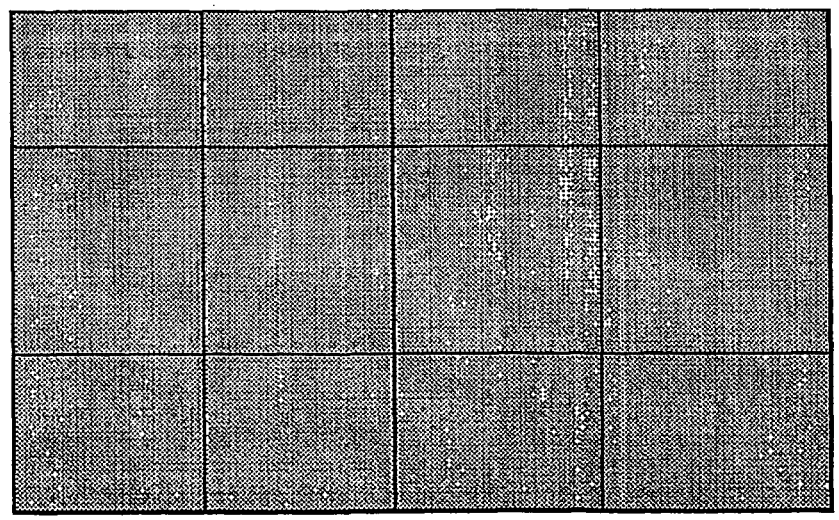

-♦- 2.5g MgSO4
-■- 2.5g MgSO4 / 7.5g Glycerol
-▲- 2.5g MgSO4 / 7.5g PEG400
-✶- 5g MgSO4 / 5g PEG400
⋯✶⋯ 5g MgSO4 / 10g PEG400
-●- 5g MgSO4 / 15g PEG400
-+- 5g MgSO4 / 10g PEG400 / 5g Glycerol
—— 4g MgSO4 / 8g PEG400 / 4g Glycerol
—— 4g MgSO4 / 12g PEG400
-♦- 3g MgSO4 / 9g PEG400

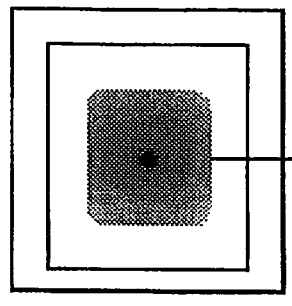
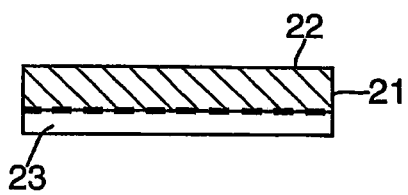
Fig.29.
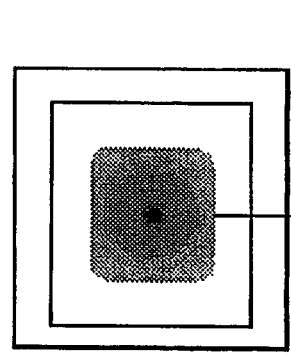
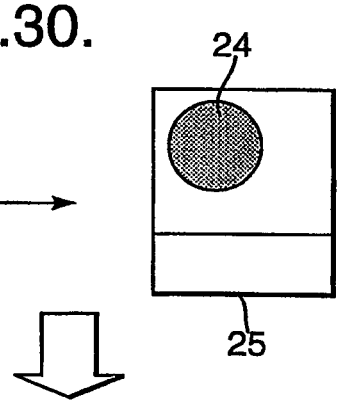
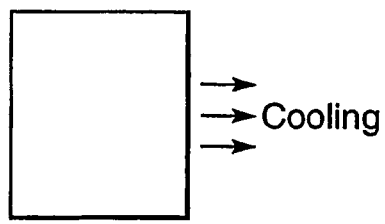
Fig.30.

EYELID MARGIN WIPES COMPRISING CHEMICAL MEANS FOR TEMPERATURE ADJUSTMENT

CROSS-REFERENCE TO RELATED APPLICATIONS

This application is a continuation, under 35 U.S.C. §120, of International Patent Application No. PCT/GB2003/004782, filed on Nov. 5, 2003 under the Patent Cooperation Treaty (PCT), which was published by the International Bureau in English on May 21, 2004, which designates the United States and which claims the benefit of Great Britain Patent Application No. GB 0225795.4, filed Nov. 5, 2002. All above-referenced prior applications are incorporated by reference herein in their entirety and are hereby made a portion of this specification.

FIELD OF THE INVENTION

The present invention relates to wipes. More particularly, it relates to eyelid margin wipes. In a further aspect, the present invention relates to a method of treatment of disorders of the eyelid margin such as those caused by meibomian gland dysfunction.

BACKGROUND OF THE INVENTION

Meibomian glands, which are positioned throughout the eyelid margins, provide lipid like secretions (known as meibum) to the surface of the eye. When blinking occurs, the upper eyelid moves downwardly over the eye and assists the lipid secretion between the margins of the eyelids. Upon eye opening, the upper lid moves upwardly and pulls a sheet of lipid upwardly to form a film over the eye. This lipid sheet coats the aqueous part of the tear layer which in turn coats the surface of the eye. The presence of this lipid sheet restricts evaporation of the tear layer such that the surface of the eye is maintained in a moist environment. Failure of the meibomian glands will mean that the required lipid layer is not properly formed and evaporation of the tear layer will occur rapidly which will lead to sensations of dryness, irritation and burning.

The main cause of failure of the meibomian glands is due to their becoming clogged. A number of factors may lead to clogging. For example, hormonal changes, particularly in levels of oestrogen, can result in thickening of the oils which will in turn clog the glands. In addition, it has been suggested that changes in oestrogen levels may cause staphylococcal bacteria, which naturally inhabit the eye, to proliferate. Unfortunately, this proliferation may cause the bacteria to invade the meibomian glands which can cause a decrease in the secretion of lipids from the glands.

Additionally or alternatively the clogging may be caused by immunological factors such as sebhorreic blepharitis or systemic diseases such as acne rosacae. Blepharitis also affects the lid margin and is often associated with meibomian gland dysfunction. Blepharitis occurs in increasing prevalence with the age of the patient. Where blepharitis occurs, inflammation of the lid margins may be noted often in combination with redness. In addition, scales, crusts and/or marginal ulcers may be observed.

Mechanical failure may also cause the glands to dysfunction. Further information relating to the aetiology of meibomian gland dysfunction may be found in Gutgessel V J et al (1982) Histopathology of Meibomian Gland Dysfunction. Ma. J. Opthal 94: 383-388.

An increased disfunction of the meibomian gland is noted with age and in addition may be seen to be higher in contact lens wearers. In Ong B L and Lark J R (1990) Meibomian Gland Dysfunction: Some Chemical, Biochemical and Physical Observations, Opthal: Physiol Opt 10: 144-148 a 30% prevalence of gland dysfunction was noted in contact lens wearers and 23% in non-contact lens wearers in a preliminary study involving 140 subjects, half of which were contact lens wearers.

In Ong B L (1996) "Relation Between Contact Lens Wear and Meibomian Gland Dysfunction" Optom & Vis Sci 73: 208-210, 231 subjects were evaluation of which 81 were contact lens wearers. A prevalence to meibomian gland dysfunction was noted in 43% of the contact lens wearers and 35% of the non-contact lens wearers.

The effect of age was considered by Hom M M et al in "Prevalence of Meibomian Gland Dysfunction 1990 Optom & Vis Sci 67: 710-712. Here 298 patients aged from 10 to over 60 were tested. The results reported an overall prevalence to dysfunction of 39%. However, the levels were low at a young age with a marked increase being noted as age increased. For each decade up to 49 years there was an increase with the maximum being at 40%. From 50 to 59 years a prevalence of 51% was noted, and for patients over 60, the prevalence was noted to have risen to greater than 67%.

In addition to contact lens wearing and aging, abnormal behaviour of the meibomian glands may be exacerbated by illness or the use of cosmetics.

The severity of meibomian gland dysfunction is variable and depends on the stages of the dysfunction. In the initial stages increased secretion is noted. This leads to over development of the epithelial cells lining the duct of the glands and to modification of the lipid composition. These cells may be excreted from the glands producing dandruff-like scales.

In the intermediate stage, the change in lipid composition leads to an increase in the melting point of the lipid, such that it becomes a paste like solid at eyelid temperature which leads to partial or total blockage of the meibomian glands. The further production and accumulation of desquamated epithelial cells adds to the blockage of the gland orifices.

In the advanced stages, long term blockage of the glands can lead to the meibomian glands becoming atrophied. It is essential to commence treatment before the final stage is reached since once the glands have become atrophic, the dysfunction is irreversible.

The slow evolutionary nature of the dysfunction means that the stages of meibomian gland dysfunction is often different for different glands along the same eyelid margin.

Conventionally, the blocked glands are treated with a cloth, facecloth or towel which is immersed in boiling water, allowed to partially cool and then placed over closed eyes. The aim of the treatment is to melt the solidified lipids and to loosen the debris which has collected around the glands and at the base of the eyelashes. It is sometimes suggested that salt should be applied to the cloth.

Whilst this treatment may be effective if correctly performed, it does suffer from certain disadvantages and drawbacks. The main drawback is that the user must estimate when the cloth is at the correct temperature before placing it over the eyes. If the cloth is too hot, there is a risk that the patient will be scalded. Conversely, if the cloth has cooled too much, the treatment will be ineffective. Further, it is a cumbersome and awkward treatment which cannot readily be utilised outside of the home. Since the procedure is complex and time consuming it is often abandoned by the patient before the required benefits are obtained. A further disadvantage of this method is that even if the cloth is at the correct temperature at the start of the treatment, it will rapidly cool such that the required temperature is only maintained for a short period of time.

An additional drawback is that there is a risk of bacterial contamination as the cloth is not sterile. This is a particularly serious problem for contact lens wearers.

A second stage of treatment is to treat the eyelid margin with cleaning agents. Examples of suitable cleaning agents are those sold under the trade marks "Lid-Care" by CibaVision and "Supranettes" by Alcon.

Whilst the use of hot cloths and cleaning agents may go some way to addressing the symptoms of meibomian gland dysfunction, there is still a need for a treatment system which will overcome the above-mentioned disadvantages and which can be readily used by patients with busy lifestyles.

Other eye problems may benefit from treatment with a hot wipe or in some circumstances with a cooled wipe. These problems include the eye symptoms encountered by hayfever sufferers and the swelling/edema caused by trauma. The application of a cooled wipe to the eye region may also be beneficial in the treatment of headaches. It is recommended that, for example for the treatment of swelling, cooling with cold water at about 8° C. for about 30 minutes is recommended. Although for ice therapy the application time may be significantly shorter. Conventionally, where the extreme treatment in which ice is applied it is necessary to take extra care to ensure that ice is not applied directly to the skin since burning can occur.

SUMMARY OF THE INVENTION

It is therefore desirable to provide a treatment which provides the user with control over the temperature and which is simple to operate.

Whilst various proposals have been made for heating bandages and the like, such as those systems described in U.S. Pat. No. 5,662,624, WO 98/29079, U.S. Pat. No. 6,465,709, WO 01/03619 and U.S. Pat. No. 6,265,631 none provide the required level of control over the temperature and maintenance of temperature. Further, they are not configured to be suitable for use in the delicate and sensitive eye area.

Thus according to the first aspect of the present invention there is provided an eyelid margin wipe comprising chemical means for adjusting the temperature of the wipe relative to the ambient temperature.

It should be noted that in general the primary function of the wipe is to clean away one or more of: dead cells; debris; meibomian secretions; and the like. Whilst in some arrangements of the present invention secretions may be adsorbed onto the surface of the wipe, in general the wipe of the present invention would not be regarded as an absorbent article.

By "adjusting the temperature" we mean that the temperature of the wipe will change relative to ambient temperature to a pre-determined temperature. The change in temperature may be a heating or cooling of the wipe.

The temperature to which the wipe will be adjusted will be dependent on the end-use to which it is to be put. However, it will be understood that by selection of the appropriate chemical means, the required temperature to achieve the desired results can be reproducibly achieved with each wipe thereby obviating the problems associated with the prior art where the cloth may not be adjusted to the correct temperature.

For the treatment of the symptoms of meibomian gland dysfunction, the required temperature is that required to melt the set lipid. As meibomian secretion is usually a mixture of lipids there is normally no sharp melting point and the various lipids present may have melting points over a wide temperature range. Ong B L and Larke J R in Meibomian Glad Dysfunction: Some Clinical, Biochemical & Physical Observations (Opthal. Physiol. Opt 1990, 10, April: 144-148) reported a range of from 32° C. to 40° C. with a significant difference in melting points being noted between normal and abnormal lipid samples.

Other experiments have suggested different temperature ranges. For example, Tiffany J M & Marsden R G in The Influence of Composition On Physical Properties of Meibomian Secretion In The Preocular Tear Film in Health, Disease and Contact Lens Wear (Dry Eye Institute, Lubbock Tx 1986; 597-608) reported a range of from 19.5° C. to 32.9° C.

These differences are attributable to the make-up of the secretion. The secretion is generally fluid enough to flow from the glands and spread to form a superficial tear film layer.

For the wipes of the present invention, in the circumstances in which the temperature adjustment is to be a rise in temperature for example for the treatment of meibomian gland dysfunction, temperatures in the region of from about 40° C. to about 55° C. will generally be desirable with temperatures in the region of from about 45° C. to about 52° C. being particularly preferred.

The adjusted temperature is preferably maintainable for at least about 5 minutes, preferably about 8 minutes and most preferably about 10 or more minutes.

For the wipes of the present invention, in the circumstances in which the temperature adjustment is to be a lowering in temperature for example to treat swelling/edema following trauma temperatures in the range of from about 0° C. to about 25° C. are desirable with temperatures in the range of about 5° C. to about 10° C. being particularly preferred. It is desirable that cooling can be maintained from about 5 minutes to about 30 minutes.

To assist the user, the wipe may incorporate an indicator which confirms to the user that the required temperature has been reached. The indicator may be a temperature sensitive colour indicator which will change colour from a first to a second colour when the required temperature is achieved. In one arrangement the colour change will be reversible such that when the wipe is no longer at the desired temperature or has fallen outside the desired temperature range the indicator will revert to the first colour. The colour indicator may be provided by any suitable means. In one arrangement at least a part of the wipe may be coated with a temperature reactive ink or treated with a temperature reactive dye. Thus the user will be advised to wait until a particular colour is achieved before using the wipe and to cease use once the particular colour disappears.

The wipe of the present invention may be of any suitable configuration. In one arrangement it may be a sheet-like material. In one alternative arrangement, the wipe may have increased thickness. The material may be impregnated with or coated with the chemical temperature adjusting means.

The wipe may be a cloth-type material. Where the wipe is formed from a cloth-type material, the cloth may be of any suitable material and may be formed by any technique including weaving, air-laying and the like. Thus the material may be woven or non-woven. The cloth may be made from natural or synthetic fibres or a mixture of both. The material may be selected for its compatibility with the chemical means used for adjusting the temperature of the wipe. Additionally or alternatively, the material may be selected for more aesthetic considerations such as softness and eye-appeal. The cloth may be of any suitable thickness. Suitable thicknesses include those from about 0.2 mm to about 5 mm, more preferably from about 1 to about 4 mm. However, thicker arrangements may be desirable in some circumstances.

In a second alternative material, the wipe, rather than being formed of a cloth-type material, may be formed from a sponge-type material. The sponge may be a natural or synthetic sponge. The sponge-type material wipe may be of any suitable size and may have a thickness greater than that noted for the cloth-type material wipe.

In a third alternative arrangement, the wipe may be provided as a multi-layered material. The material in each layer may be the same or different. For example, the wipe may comprise a sponge material having attached to one or both surfaces thereof a cloth-type material. Where the cloth-type material is applied to two opposing faces of a sponge-type material, the material used in each face may be the same or different. The multi-layered wipe may be of any suitable thickness.

The wipe may comprise several layers of cloth-type material, each of which may be different. Where a layered structure is used, the temperature adjusting means may be located in or on one or more of the layers.

Where the wipe is to be coated with one or more temperature adjusting materials, it may be coated on one or both sides of the wipe. However, the chemical means is preferably only applied to one side to allow an uncoated free side of the wipe. In some arrangements the uncoated side may be applied to the eye. In alternative arrangements, the uncoated side may be used for application of materials such as therapeutic materials, cleaning fluids or the like.

Where the wipe is impregnated with temperature adjusting material, the material may be located throughout the wipe or, for example, may be provided in such a manner that particles of the temperature adjusting material will not come into contact with the eye when in use. The temperature adjusting material may be immobilised in a non-woven pad which is provided, for example, as the cloth-type material or as one layer in a multi-layered arrangement.

In a further alternative arrangement, or where required by the temperature adjusting means selected, the wipe may be an arrangement comprising a pocket or the like into which the temperature adjusting components may be placed, either directly or in a separate container. In an alternative arrangement the material from which the wipe is formed surrounds the temperature adjusting means, for example is wrapped around the temperature adjusting means which may be placed in a suitable container.

The temperature adjusting component may be a self-heating or cooling device or a device relying on external sources of heat or cold. Where external devices are used to cause the temperature adjusting means to change temperature, these may be conventional sources such as ovens, microwave ovens, refrigerators and the like. In one alternative arrangement, the external device may be a purpose-built device. In one arrangement, the chemical temperature adjusting means may be activated by a conducting foil-strip located in the wipe which may be connected to an energy source.

The wipe is preferably single use but in one alternative, although not-preferred, arrangement, the wipe may be re-usable. Where multi-use is desirable, the wipe will generally be configured such that it comprises a pocket for containing the temperature adjusting means which is preferably located in a separate container. On re-use, the temperature adjusting means container will generally be removed and replaced with a fresh container. Where the wipe is to be re-used in this manner, it is preferably produced from washable material.

The wipe may be of any suitable shape and/or configuration. Suitable shapes include squares, rectangles, circles and ovals. In one arrangement, the wipe may be finger-shaped. The wipe may be of any suitable size. It may be sized to be approximately the size of one eye region or may be sized such that it could be used on two eyes simultaneously. In this latter arrangement, a band, such of elastic, may be provided so that the user can wear the wipe for a period of time.

The wipe may be shaped to have a profile which assists its operation. For example, the wipe whether of a square, rectangular, cicular or ovoid shape may be curved such that when laid over the closed eye, it will follow the curvature of the eye and ensure that the temperature is provided across the entire eyelid and eyelid margin.

In one arrangement the wipe may be coated, at least on one surface, with a material, such as a polymeric material which is soft such that it moulds to the shape of the users eye and thereby ensures that the temperature is provided across the entire eyelid and eyelid margin. In one arrangement the polymeric material may not be soft at room temperature but softens as the temperature of the wipe increases.

In one preferred arrangement the wipe may include a pocket into which the user may insert one or more fingers. This arrangement will facilitate the user when performing any rubbing of the eyelid margin which may be desirable, for example as part of the treatment of meibomian gland dysfunction. In a most preferred arrangement, the wipe may be shaped to correspond to the shape of a finger. One benefit of this arrangement is that the user will be able to readily control the wipe during any rubbing motion.

In one alternative arrangement, the configuration of the wipe may correspond to two or more finger shapes, conjoined, for example by a web of material. In one arrangement, each fingered shaped portion would be arranged to receive at least part of one finger. In a preferred arrangement of the present invention one or more finger portions would include the heating means and one or more other finger portions would be of non-heated fabric which might be used for massaging or for the application of, for example, cleansing agent.

In one arrangement, the wipe, however configured, may include an adhesive portion so that it can be left in place on the eye to warm or cool the eye prior to massaging taking place. In one arrangement, the adhesive portion may comprise at least a part of one side of the wipe. In one alternative arrangement the whole of one side may be adhesive. In this arrangement, the user will normally turn the wipe over prior to massaging/wiping such that massaging/wiping is carried out with a non-adhesive side of the wipe. Where an adhesive portion is used, the wipe will generally be provided with a removal strip, such as a polymer strip or a paper strip surface treated with silicone, in place to protect the adhesive material. Any suitable adhesive material may be used which enable the wipe to be held in place without causing irritation to the delicate eye area and which will enable the wipe to be readily removed without causing discomfort to the user. Examples of adhesive materials include acrylic adhesives, liquid absorbing adhesives, such as a hydrocolloidal or hydrogel adhesives, natural rubber or synthetic rubber.

The adjustment in the temperature of the eyelid wipe may be achieved by any suitable means. However, the selection of the appropriate means will generally be dependent on the required temperature for the wipe and the suitability of any chemical components for use in the delicate eyelid region. The ability of the material to maintain the temperature for the required period of time may also be a factor which will be taken into consideration when selecting the heat adjusting means. Where chemicals are to be used which are not suitable for direct application to the skin or eyelid margin, the arrangement in which the heat adjusting means are placed in a separate container within the wipe will generally be utilised, although any means for separating them from the skin may be used.

The method chosen to accomplish the adjustment in temperature preferably enables the wipe to reach the desired temperature in a short period of time, usually less than about 60 seconds. Times in the order of from about 30 to about 60 seconds are particularly preferred.

In one arrangement, the wipe, however configured, may alter in temperature on exposure to oxygen, generally the oxygen in the air. Examples include the use of wipes impregnated with, or coated with, material which on exposure to air oxidises and in doing so generates heat. In one arrangement, the material which on exposure to air oxidises to generate heat may be placed in an oxygen-permeable bag which may be enclosed within the wipe or placed in a pocket in the wipe.

Suitable materials include those which form an oxide when reacted with oxygen at room temperature including: iron, aluminium, magnesium, titanium, manganese, zinc, molybdenum and tin oxide (II) with iron powder being particularly preferred. The material will generally be provided in powder form to provide a large surface area on which oxidation may occur. The material used may be a mixture of two or more of the foregoing. Further examples of suitable materials include: metal sulphides, polysulphides or hydrosulphides mixed with a catalyst carried on a carbonaceous material; powdered solids such as elemental iron, mixed with salts and water; mixtures of iron powder, water, cellulose, salt and vermiculite activated carbon; iron powder, water, salt and activated charcoal; iron or other metals mixed with alkali metal salts and a catalyst; redox systems such as metal powder (usually ferrous), a metal chloride, water and a water absorber; and alkaline earth metal oxides, such as magnesium oxide, with chlorides or sulfides of alkali metals or alkaline earth metals. It will be understood that some of the components of the mixtures listed do not directly contribute to the heat generating reaction but are present to modify or control the reaction. For example, catalysts, assistants, fillers and moisteners may be present.

Where the temperature adjustment means operates on exposure to air, the wipes will generally be provided to the user in an airtight package. Examples of airtight packages include plastic envelopes and foil, particularly aluminium foil, pouches. As the package is opened, the wipe will be exposed to air and the adjustment in temperature will commence.

In one alternative arrangement, the wipe, however configured, may alter in temperature on exposure to water. In this arrangement, material impregnated into, coated on, or enclosed within the wipe may be based on chemical substances which generate heat when in the presence of water. The heat generated may be, for example, heat of hydration, dissolution or oxidation. The material which generates heat on contact with water may be placed in a water-permeable bag which may be enclosed within the wipe or placed in a pocket in the wipe.

In use, these wipes would need to be treated with water, or an aqueous solution in order for the heat to be generated. Suitable aqueous solutions include saline, potassium salts, calcium salts, aluminium chloride, calcium chloride, magnesium chloride, potassium sulphate, magnesium sulphate, sodium sulphate and the like. Other solutions may also be used to "wet" the wipe, including those solutions commonly used in contact lens care regimes. The water or other solution may be applied by immersing the wipes in the water or solution or the water/solution may be poured or sprayed onto the wipe.

Suitable materials for altering the temperature of the wipe when contacted with water or other suitable solution include sodium hydroxide, cobalt, chromium, iron, iron hydroxide, magnesium, manganese, molybdenum, tin oxide (II), titanium and calcium hydroxide. These powdered solids may be used alone or in combination. Also suitable are powdered solids such as iron. These may be used alone or with other components such as salt and activated charcoal, or with alkali metals salts and a catalyst. In addition, hydratable organic or inorganic salts such as calcium chloride, calcium sulfate, cerous chloride, sodium carbonate, aluminum chloride, magnesium chloride, magnesium sulfate, zinc citrate, zinc sulfate, zinc nitrates, alkali metal carbonates, alkali metal borates, alkali metal acetates, alkali metal citrates or alkali metal phosphonates may be used. Similarly mixtures such as: anhydrous calcium chloride, cerous chloride, cesium hydroxide, sodium carbonate and organic oxide or salts such as calcium oxide, aluminium chloride or calcium nitrate; sodium chloride with an organic oxide or salt; hypochlorite salts with cellulosic or cellulosic-containing materials; anhydrous calcium chloride and calcium oxide; anhydrous calcium chloride, anhydrous sodium acetate and calcium oxide; boron compounds having a boron-oxygen-boron bond; anhydrous glycol; silica gel; activated alumina; and synthetic zeolites may be used. Anhydrous zeolites, hydratable organic or inorganic salts, magnesium sulphate, magnesium chloride, calcium chloride and calcined gypsum are particularly preferred. Each of these would produce an exothermic reaction when mixed with water.

Also suitable are ammonium nitrate, sodium nitrate, ammonium sulphurate, potassium nitrate, sodium thiosulphate, ammonium chloride, ammonium bromide, ammonium iodide, potassium chloride and tin chloride dihydrate which each produce an endothermic reaction when mixed with water.

Whichever method is used to alter the temperature, additional materials may be used to control or extend the reaction.

In a further alternative arrangement, the wipe may contain two components which are kept separate until temperature adjustment is required at which time they are allowed to mix.

This technology may be provided by placing one of the components in a frangible container which may be enclosed within the wipe or, where appropriate, the wipe may comprise a pocket for holding a container comprising one of the components or a container comprising both components separated by any suitable means. In one alternative arrangement, a single container may be used which comprises two or more chambers, each containing one component. When required, the components may be mixed, for example, by the breakage of a frangible seal separating the two chambers such that a reaction between the two components can occur. Where the reaction is an exothermic reaction, heating will occur. Similarly where the reaction is an endothermic reaction, cooling will be achieved.

The container may be made of any suitable material. Where the component to be included in the container is water or an aqueous solution, the material from which the component is manufactured will be water-impermeable. Any suitable water-impermeable material may be used provided that it has the sufficient level of brittleness to rupture when pressure is applied. Suitable materials include polymers such as polyethylene, polypropylene, polyvinyl acetate, polyurethane, silicone rubber and polyvinyl chloride.

The container may be constructed such that the contents can be delivered to the other component in a pre-determined and controlled manner, such that the temperature change can be maintained for the desired period of time. For example, the container may be a flexible container having sealed orifices which open when pressure is applied to the container. The size of the orifices will determine the time period over which the component will be released from the container.

In an alternative arrangement one of the components may be located on the wipe or may be impregnated in the material of the wipe and the other component may be located within a container which is frangible or which has a frangible seal, and which is located within the wipe or within a pocket in the wipe.

In one example of a two component system, the first component may be a compound which generates heat on contact with water, such as calcium oxide, anhydrous magnesium sulphate, colloidal clay or any other of the compounds identified as generating heat on contact with water above and the second component, separated from the first, may be water, saline or other aqueous solution, including surfactant solutions. The second component may additionally include active agents such as anti-inflammatory or anti-bacterial agents.

Other two component systems include: magnesium/iron alloys and electrolytes (suitable electrolytes include saline); magnesium chloride with ethylene glycol; sodium thiosulfate with ethylene glycol; boron-compounds having a boron-oxygen-boron bond with a protic material such as water, methanol, ethanol, propanol, isopropanol, butanol, lower amines, lower alkanol amine, aliphatic oxides and polyols.

In another example of a two component system, the first component may be a compound which cools down on contact with water such as sodium nitrate and the second component separated from the first until activation of the device may be saline, water or other aqueous solutions such as surfactants. The second component may additionally contain active agents such as anti-inflammatory or anti-bacterial agents.

A further example of a two component system is an oxido-reduction system in which an oxidising agent and a reducing agent are used which undergo reaction when combined to generate heat. Examples of oxidising agents include hydrogen peroxide, urea hydrogen peroxide, sodium peroxide, sodium perborate, sodium persulfate, ammonium persulfate and potassium persulfate. Examples of reducing agents include thiourea compounds such as 1-phenyl-2-thio-barbituric acid. Preferred reactions include: a hydride such as an alkali metal or alkaline earth metal borohydride such as sodium, potassium or calcium borohydrides with an aldehyde such as glyceraldelyde, a ketone such as acetone, a peroxide or a sulfoxide; thiooxypyrimidine or 2-thio-4 oxypyrimidine with hydrogen peroxide or sodium perborate; thiourea with hydrogen peroxide; or alkali metal salts or manganese and chromium oxides such as potassium permanganate or potassium chromate and alcohols or polyols such as glycerin.

A still further example of a two component system includes the reaction between an aqueous salt solution, such as aqueous sodium solution, and seed crystals or metallic triggers that, on contact with the aqueous salt solution, will activate crystallisation and thereby generate heat. Examples include aqueous sodium acetate solution and sodium acetate seed crystals. One benefit of using a system in which crystallisation occurs is that the presence of the resultant crystals within the wipe may be beneficial during massaging of the eye. Some reactions in a two component such as magnesium sulphate and water, a first exothermic reaction will occur followed by a crystallisation which will also generate heat thereby prolonging the heating of the wipe.

Whichever systems are used to adjust the temperature of the wipe, materials may be present to regulate the reaction that causes the adjustment of temperature. Suitable materials include gelling agents, polymers and the like.

It will be understood that some mixtures identified include materials which do not contribute to the heat adjusting reaction but are adjuncts present to control the reaction. Similarly, materials may be present to extend the temperature adjusting reaction. For example, where the heat adjusting reaction is an exothermic reaction, water-containing material that will release water above a particular temperature may be present.

In addition, physical means may be included in the wipe to control the temperature delivered to the user. For example, one or more insulating layers, may be included. Similarly one or more diffusing layers may be incorporated. In one alternative arrangement a covering may be applied to the wipe which assists in the temperature control. The thickness of the one or more layers in the wipe may be selected to assist with temperature control.

Thus, the wipe may include a reflective layer and/or a conductive layer to direct the heating or cooling towards one surface of the wipe. The reflective layer and/or the conductive layer may be made of any suitable material. Examples of suitable materials include metal foils such as aluminium foil. Also suitable are amorphous metallic oxide layers which are very thin and which may be translucent.

The layered wipe including for example diffusion layers, insulating layers and the like and the heat adjusting means located in a container, may have any suitable thickness but will generally be in excess of about 5 mm.

It will be understood that whatever method of heat control is selected, by selection of particular chemical reactions, a required temperature can be achieved and controlled without any decisions having to be taken by the user. In addition the structure of the wipe can be selected to optimise the temperature and control its application to the user.

A further advantage of the present invention is that the chemical means may be selected such that the required temperature can be maintained for sufficient time to allow effective treatment to be carried out.

Further, since the reaction will be reproducible in each wipe containing the same temperature adjusting means, the user can be assured of the appropriate temperature to achieve efficacy at each treatment without the risk of burning of the delicate skin in the eye region.

Whilst the present invention is described with particular reference to the treatment of meibomian gland dysfunction, it will be understood, that dependent on the temperature of the wipe, there may be a variety of uses. For example, a cooled wipe may be useful in the treatment of the symptoms of, for example, hay fever. The wipes may also be useful in the lid care of contact lens wearers and the sufferers of dry eye and also in the removal of eye cosmetics. In this latter arrangement, in addition to the heat management means, the wipe may include solutions particularly suitable for the removal of eye make-up and/or having lipid solubilising properties.

The eyelid wipe may be provided in a sealed pack formed from any suitable material. Examples of suitable materials include plastics and metal foils. The wipe is preferably sterile.

Where the temperature adjusting means is immobilised in the wipe rather than being placed in a container within the wipe or a pocket in the wipe a binder may be used. Suitable binders include cellulose polymers, polyacrylic polymers, polyurethanes polymers, gelatins and gums. Specific examples include hydroxymethylcellulose, hydroxyethylcellulose, hydroxypropylcellulose, cellulose acetates, polyvinylidene and copolymers of polyacrylic acid and polyacrylates.

Whilst the foregoing discussion relates to the temperature adjusting means being located within the wipe, the temperature adjusting means may be located within the packaging in which the wipe is provided. Any of the arrangements detailed herein may be incorporated within the packaging. In use, the user will activate the chemical adjusting means while the wipe is within the packaging, allow the wipe to reach the required temperature and then remove the wipe from the packaging for use. In this arrangement, the wipe will generally be formed from a cloth-type material.

In a preferred arrangement, the eyelid wipe will additionally be impregnated with cleansing agents, surfactant agents or cleansing and surfactant agents. The surfactants may be effective as cleaning agents and/or solubilising agents. Any suitable cleansing or surfactant agents may be used and examples include PEG-80 sorbitan laurate, sodium trideceth sulfate, PEG-150 distearate, cocamidopropyl hydroxysultaine, sodium laureth-13 carboxylate, disodium lauroamphodiacetate, polysorbate 80, polysorbate 20, poloxamer 184, ammonium laureth sulfate, ceteareth 20,25, cocamidopropyl betaine, disodium laureth sulfosuccinate, disodium lauriminodipropionate, disodium lauroamphodipropionate, glycol stearate, hydrogenated castor oil, laureth-23, magnesium laureth, oleth sulfate, PEG-20 stearate, PEG-35 castor oil, PEG-40 hydrogenated castor oil, PEG-60 hydrogenated castor oil, PEG-7 hydrogenated castor oil, PEG-75 lanolin, poloxamers, sodium laureth sulfate, sodium trideceth sulfate, sodium C12-15 pareth 15 sulfonate, and sodium C14-16 olefin sulfonate.

Thus the invention in preferred embodiments provides for the controlled delivery of an appropriate temperature with controlled delivery of agents such as cleaning agents, surfactant agents or soothing agents.

The wipe may also include one or more of antistatic agents, preservatives, antioxidants, antimicrobial agents, chelating agents, emollients, emulsifying agents, buffering/neutralising agents, humectants, thickeners/viscosity controlling agents and antistatic/conditioning agents.

One example of a suitable preservative is imidazolidinyl urea. Suitable antioxidants include tocopherol and tocopheryl acetate. Suitable antimicrobial agents include quaternium-15. EDTA is one example of a suitable chelating agent. Sodium methylparaben, sodium propylparabem and quaternium 8,14 may also be present.

Examples of emollients include natural or mineral oils or esters. Specific examples include potassium C12-13 monoalkyl phosphate polysorbate 60, potassium C12-13 monoalkyl phosphate, calendula officinalis, almond oil PEG-6 esters, capric/caprylic triglyceride, cetearyl alcohol, cocoa butter, decyl oleate, dimethicone, dimethicone copolyol, glyceryl stearate, glyceryl caprylate, glyceryl oleate, glycol stearate, glycol oleate, hydrogenated castor oil, hydrogenated soybean oil, laneth-10 acetate, lanolin, lanolin alcohol, acetylated lanolin alcohol, lecithin, PEG-11 castor oil, PEG-75 lanolin, petrolatum, PPG-26 oleate, PEG-10 butanediol or stearyl alcohol.

Examples of emulsifying agents include PEG-6 caprylic/capric glyceride, ceteareth 20,25, cetearyl alcohol, glycereth-20 stearate, glyceryl stearate, glyceryl caprylate, glyceryl oleate, glycol stearate, glycol oleate, hydrogenated castor oil, laneth-10, laneth 10 acetate, lanolin, lanolin alcohol, laureth-23, lecithin, PEG-20 stearate, PEG-150 distearate, PEG-40 hydrogenated castor oil, PEG 60 hydrogenated castor oil, PEG 7 hydrogenated castor oil, PEG-11 castor oil, PEG-35 castor oil, PEG-15 tallow polyamine, PEG-75 lanolin, poloxamer, polysorbate 20,80, sodium laureth-13 carboxylate, sodium trideceth sulfate and stearic acid.

Examples of buffering/neutralising agents include dipotassium phosphate, sodium hydroxide, potassium phosphate, disodium phosphate, citric acid, aminomethyl propanediol, sodium hydroxide, diethanolamine bisulfate, ethanolamine, hydrochloric acid, lactic acid, sodium phosphate and triethanolamine.

Examples of humectants include propylene glycol, glycereth-20, glycerin, hyaluronic acid, inositol, lactic acid, methyl gluceth-20, PEG-8, PEG-20 stearate, sodium PCA and sorbitol.

Examples of thickeners/viscosity controlling agents such as carbomers, caprylic alcohol, cetearyl alcohol, dextran, disodium lauroamphodiacetate, guar gum hydrogenated castor oil, laneth-10, magnesium sulfate, PEG-150 distearate, stearyl alcohol and xanthan gum.

Examples of antistatic/conditioning agents include dimethicone copolyol, disodium lauriminodipropionate, disodium lauroamphodiacetate, disodium lauroamphodipropionate, glycol oleate, hyaluronic acid, inositol, lanolin, lanolin alcohol, lecithin, panthenol, PEG 15 tallow polyamine, petrolatum, polyquaternium 7,11,16,44 and sodium PCA.

The wipes may additionally or alternatively be impregnated with one or more of the commercially available cleansing agents including those sold under the trade names "LidCare" available from CibaVision, "Eye-Scrub" available from Novartis Opthalmics, "Lid Scrub", "Igiene Daily Eyelid Cleanser" available from Igenics, "Blephasol" available from Laboratoire Théa and "Supranettes" available from Alcon.

Additionally or alternatively, the eyelid wipe may be impregnated with active agents such as anti-inflammatory and anti-bacterial agents and/or decongestants. The use of the combination of heating, optionally also with cleaning, at the time that the active agents are applied to the eyelid, is believed to improve the efficacy of the active agents. It will therefore be understood that in this embodiment, the invention provides the controlled delivery of an appropriate temperature with controlled delivery of the appropriate amount of active agent, optionally with controlled delivery of the required amounts of cleansing solution.

In one arrangement, one or more of cleansing agents, pharaecutical compositions, active agents and the like may be located in a layer on the outersurface of the wipe which is formed from a thermo-responsive polymer which on heating would soften so that the polymer matrix will reduce the active agent.

In one preferred arrangement, the temperature adjusting means provide cooling and one or more active agents such as anti-inflammatory agents, anti-bacterial agents and/or decongestants are present. Such wipes are particularly useful in the treatment of the symptoms of, for example, hayfever.

The wipe may include, or may be combined with, a drug delivery system such that there is achieved a system which enables the controlled delivery of an appropriate temperature in combination with controlled delivery of a pharmaceutical.

It will be understood that care will be taken in the selection of heat adjusting means and any other components present to ensure that components and products of reaction are not liable to cause damage to the delicate eye region. Where a selection is made where direct contact with the eye region is not advisable, the materials will generally be enclosed within a container in the wipe.

Where the wipe is multi-layered, or where the wipe includes a container for one or more of the components of the chemical heat adjusting means, the edges of the wipe may be sealed either directly or via an intermediate sealing means. Any suitable means of sealing may be used. Suitable means include the use of adhesive, including hot melt and pressure sensitive adhesive, double sided adhesive tape, heat sealing or ultrasonic bonding. In general, the sealing means will be selected such that there is no hard residue which would be uncomfortable when the wipe is in use.

The present invention also provides the use of the wipe of the above-mentioned first aspect in the treatment of disorders of the eyelid or eyelid margin. In a preferred arrangement of this second aspect of the present invention, there is provided the use of the wipe of the above-mentioned first aspect in the treatment of meibomian gland disorder. In an alternative arrangement of this second aspect of the present invention, there is provided the use of the wipe of the above-mentioned first aspect in the treatment of inflammation of the eyelid. In this arrangement, the temperature adjustment of the wipe is preferably cooling.

In a further aspect of the present invention, the application also provides a method of treating meibomian gland dysfunction and/or blepharitis comprising allowing the wipe of the above first aspect to reach temperature and then massaging the eyelid margin with the wipe. Cleansing agents or the like may be applied to the wipe before massaging is commenced.

In use, it may be desirable for the user to leave the wipe against the eye for a short period prior to commencing massaging of the eyelid margin with the wipe. The period of time required may be of the order of about 5 minutes to about 10 minutes.

BRIEF DESCRIPTION OF THE DRAWINGS

The wipe of the present invention will now be described by way of example, with reference to the accompanying drawings in which:

FIG. 1 illustrates a circular wipe with heat delivery system;
FIG. 2 illustrates a tubular wipe with heat delivery system;
FIG. 3a illustrates an alternative tubular wipe with heat delivery system;
FIG. 3b illustrates a modification to the tubular wipe of FIG. 3a
FIG. 4a illustrates an ovoid shaped wipe with an alternative heat delivery system;
FIG. 4b illustrates an alternative arrangement for the ovoid shaped wipe;
FIG. 5 illustrates a folded cloth-like wipe;
FIG. 29 is a schematic representation of the wipe of Example 51;
FIG. 30 is a further schematic representation of the wipe of Example 51 at activation.

DETAILED DESCRIPTION OF THE PREFERRED EMBODIMENT

Figure 6:
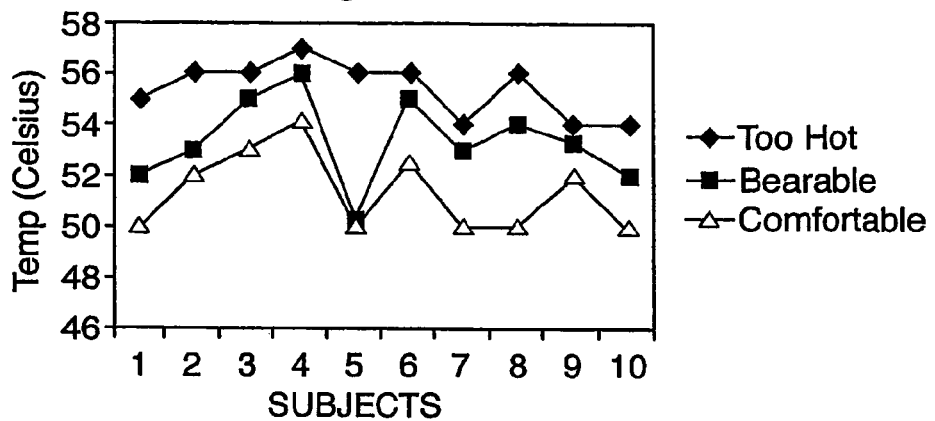
FIG. 6 is a graph representing the results of Comparative Example 2.

In one embodiment of the present invention as described in FIG. 1, the wipe 1 is of circular configuration and is formed from a layered structure. The layers present comprise a porous outer layer 2, a layer 3 impregnated with cleaning agent, a heat generating layer 4 comprising material which on exposure to air or water generates heat. This layer is optionally backed by a heat reflective layer 5 which serves to direct the heat released by the heat generating layer 4 towards the outer layer 2. These layers are supported on a holding layer 6 which is generally cloth-like and will form the outer layer which the user will hold in their hand. The wipe 1 will generally be sealed around the edge. The edge margin may comprise solely the porous outer layer 2 and the holding layer 6 bonded together.

As illustrated in FIG. 2, the wipe 1A may be provided as a tube into which the user may insert a finger to facilitate the massaging step required in use. Here the wipe 1A is formed in a similar manner to the circular wipe of FIG. 1. It will generally be formed as a rectangular material comprising a porous outer layer 2, a layer impregnated with cleaning agent 3, a heat generating layer 4, a heat reflective layer 5 and a holding layer 6. When this rectangle is formed into a tube, the holding layer 6 becomes the inner wall of the tube. In this arrangement, the inner wall may be cloth-like or sponge-like.

A modification of the tubular wipe is a wipe having a closed end so that the user's finger does not protrude through the wipe. The wipe 1B may have the same configuration throughout the sides of the wipe such as in the tubular arrangement of FIG. 2 as illustrated in FIG. 3B or in the alternative arrangement illustrated in FIG. 3A the wipe may have a side A' which will, in use, be placed against the eye. The user would normally have this side located on the inside of their finger. The wipe of FIG. 3B will also have a plain holding layer B' for the exterior of the finger. In this arrangement the side A' of the finger wipe will have a similar structure to that of the circular wipe of FIG. 1.

An alternative arrangement is illustrated in FIG. 4a. In this arrangement, the wipe 1C has an ovoid configuration to mirror the overall eye shape. In the centre of the ovoid is a pressure point 7 which when pressed activates the chemical reaction. In this wipe, a two-component means is used to cause the adjustment of temperature. The wipe contains an inner breakable pouch 8 which in A contains seed crystals and in B a metallic trigger. When the user depresses the wipe at the pressure point 7, the pouch breaks such that the seed crystals/metallic trigger come into contact with an aqueous salt solution in which the wipe is first soaked. The wipe of FIG. 4 additionally comprises an optional self-adhesive layer 9. As illustrated in FIG. 4b the pressure point 7 may be located to one side of the wipe.

In FIG. 5, the wipe 1D, which on this occasion is a folded cloth-like wipe impregnated with substances which will generate heat when treated with an aqueous solution. Cleaning agents are also impregnated into the wipe. The folded wipe is provided in a moisture impermeable pouch 10.

The invention will now be described with reference to the following examples.

COMPARATIVE EXAMPLE 1

Determination of Target Temperature for a Hot Wipe in Particular for Use in the Treatment of Meibomian Gland Dysfunction A cloth was immersed in boiling water and then removed. The temperature of the cloth was measured and the skin tolerance to the cloth was evaluated. The skin tolerance was evaluated by placing the cloth on the inside of the wrist. It was found that the temperature reached was much higher than was acceptable in terms of skin tolerance and that therefore if such a cloth were to be used as a hot compress in the treatment of, for example, meibomian gland dysfunction, there was a risk that injury could occur to the patient. The tolerance level was found to be in the region of 53° C. Temperatures of 43° C. and below were said by the subjects to be not hot enough for any beneficial effect to be felt. The results are summarised in Table 1

TABLE 1

| WARM CLOTH | Temperature |
| --- | --- |
| Out of boiling water | approx 63° C. |
| Max tolerable to skin | approx 52-53° C. |
| "Not hot enough" (skin) | approx 43° C. |

COMPARATIVE EXAMPLE 2

Comparative Example 1 was repeated using a cloth impregnated with heated saline solution. The compress was applied to a closed eye to mimic the routine used by a patient following the conventional treatment for meibomian gland dysfunction. The average results for 10 subjects are summarised in Table 2 below and in the graph of FIG. 6.

TABLE 2

| WARM CLOTH | Temperature |
| --- | --- |
| "Too hot" | approx >54° C. |
| "Bearable" (eye area) | approx 53° C. |
| "Comfortable" (eye area) | approx 51° C. |

Thus it was noted that a temperature of above 54° C. was uncomfortable. It was often expressed as being too hot for the subjects. The optimal temperature was found to be in the region of 51° C. Thus a temperature range of from about 45° C. to about 52° C. is preferred. For maximum efficacy the temperature should be sustained for 10 minutes.

Various formulations for the chemical temperature adjusting means were investigated.

EXAMPLE 1

Air Triggered System

Figure 7:
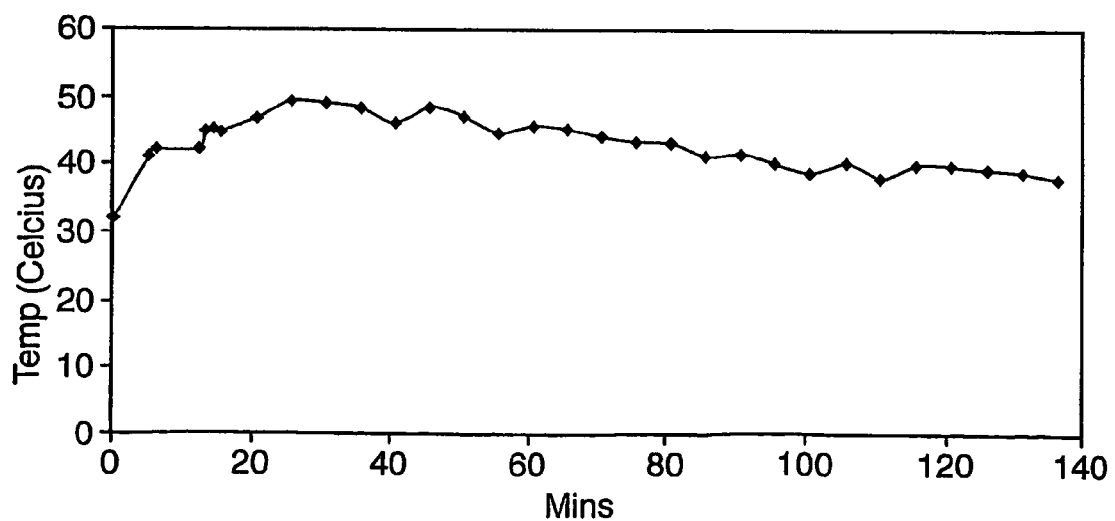
FIG. 7 is a graph representing the temperature changes noted for the formulation of Example 1.

A sealed pouch was prepared into which a powder comprising 59% iron powder, 21% water, 10.5% vermiculite, 4% activated charcoal and 5% salt had been placed. The pouch was opened and the temperature changes were noted. These are represented graphically in FIG. 7.

EXAMPLE 2

Water Triggered System A

Figure 8:
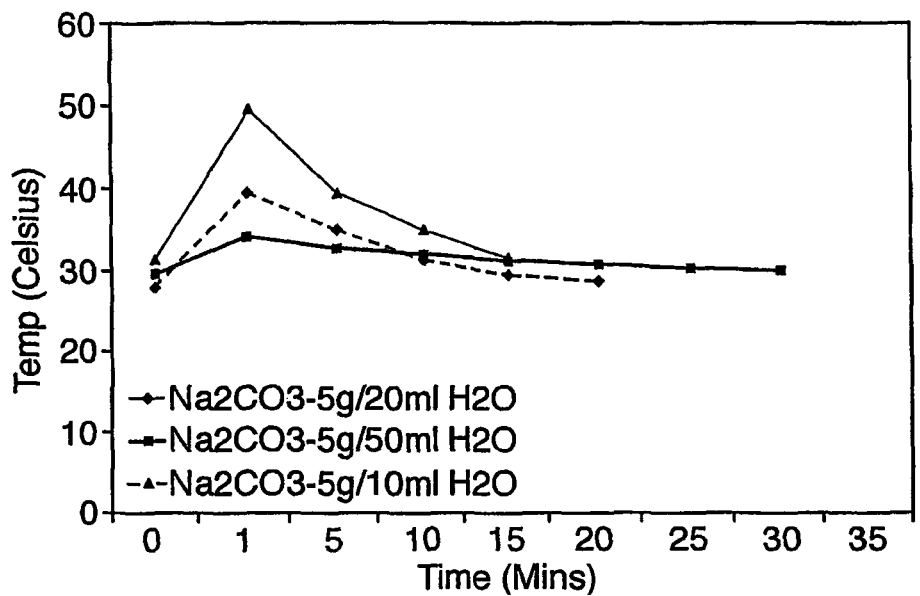
FIG. 8 is a graph representing the temperature changes noted for the formulation of Example 2.

A sealed pouch was prepared into which anhydrous sodium carbonate had been placed. Water was added to the pouch and the temperature changes were noted. These are represented graphically in FIG. 8.

EXAMPLE 3

Water Triggered System B

Figure 9:
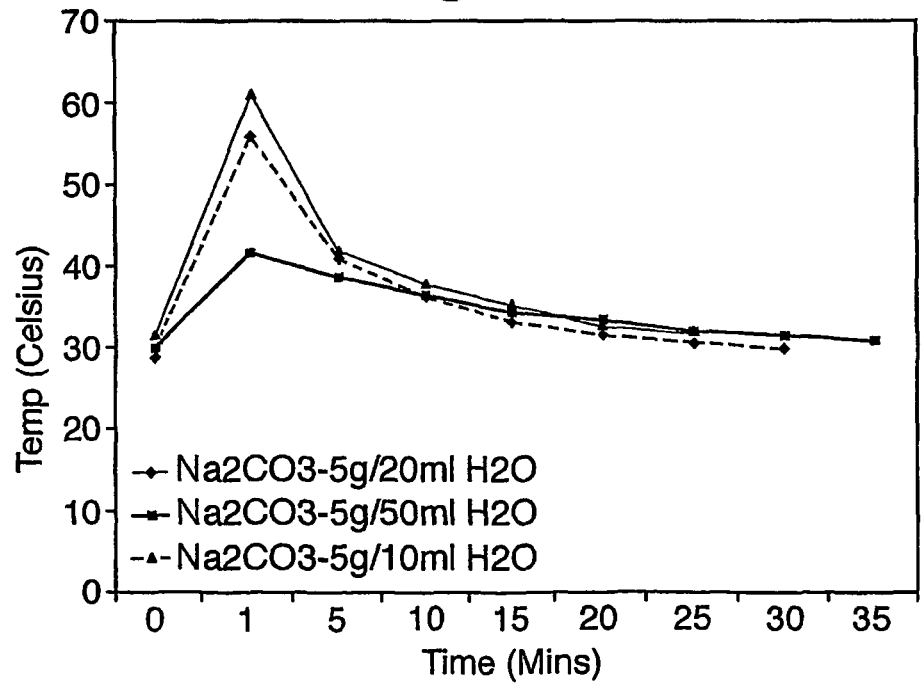
FIG. 9 is a graph representing the temperature changes noted for the formulation of Example 3.

A sealed pouch was prepared into which anhydrous magnesium sulphate had been placed. Water was added to the pouch and the temperature changes were noted. These are represented graphically in FIG. 9.

EXAMPLE 4

Water Triggered System C

Figure 10:
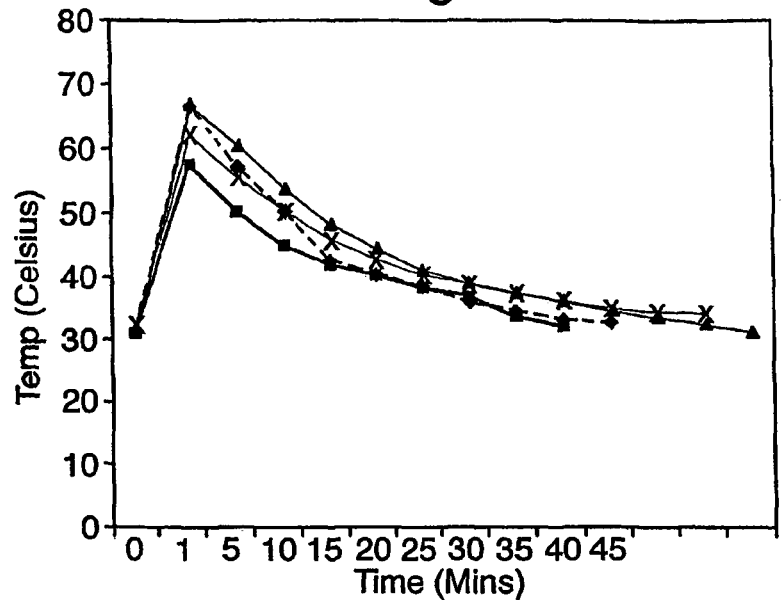
FIG. 10 is a graph representing the temperature changes noted for the formulation of Example 4.

A sealed pouch was prepared into which anhydrous magnesium sulphate (25% w/w) and propylene glycol (75% w/w) or PEG400 (75% w/w) had been placed. Water was added to the pouch and the temperature changes were noted. These are represented graphically in FIG. 10.

EXAMPLE 5

Water Triggered System D

Figure 11:
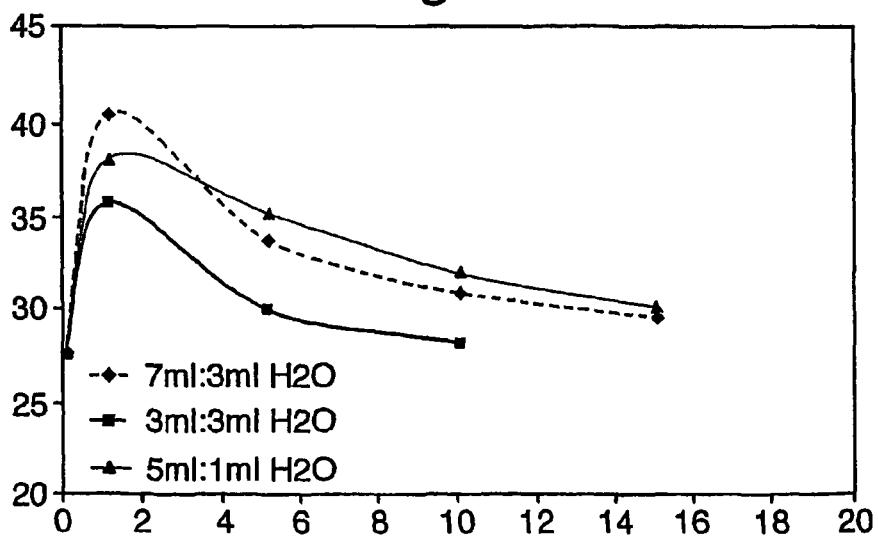
FIG. 11 is a graph representing the temperature changes noted for the formulation of Example 5.

A sealed pouch was prepared into which anhydrous sodium potassium aluminosilicate 3 Å (35% w/w), PEG200 (55% w/w) and glycerin (10% w/w) had been placed. Water was added to the pouch and the temperature changes were noted. These are represented graphically in FIG. 11.

EXAMPLE 6

Two component system A

Figure 12:
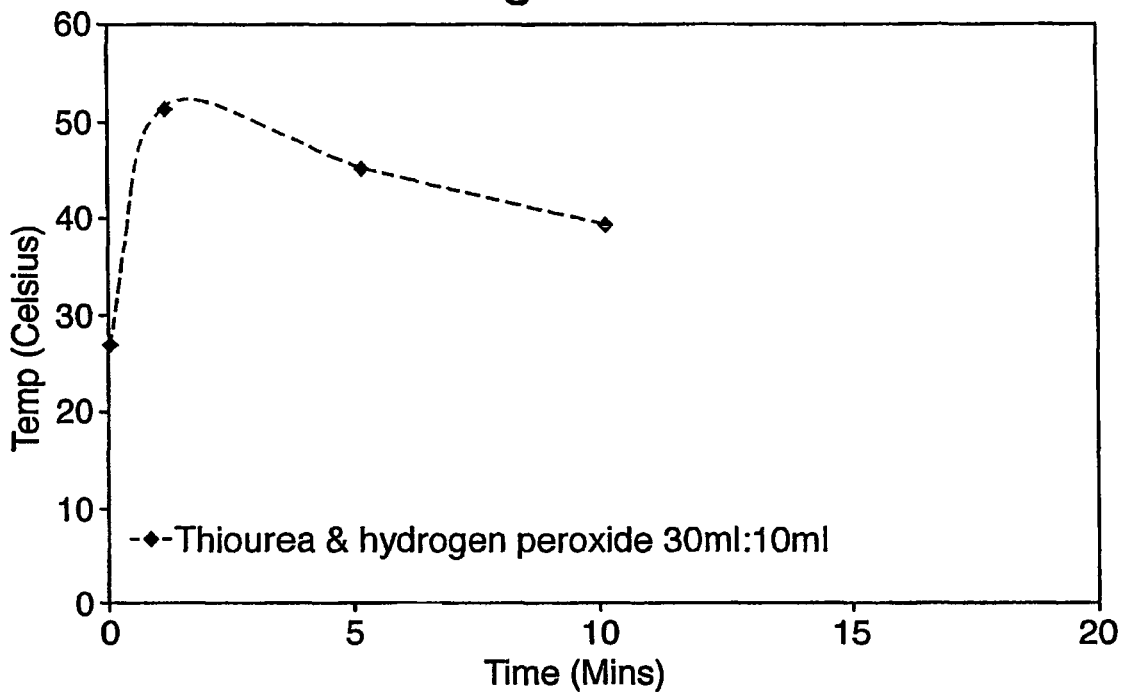
FIG. 12 is a graph representing the temperature changes noted for the formulation of Example 6.

A two component system was prepared. The first component comprised the reducing agent thiourea and the second comprised the oxidation agent hydrogen peroxide solution (approx 8%). The two components were mixed and the temperature changes were measured. These are represented graphically in FIG. 12.

EXAMPLE 7

Figure 13:
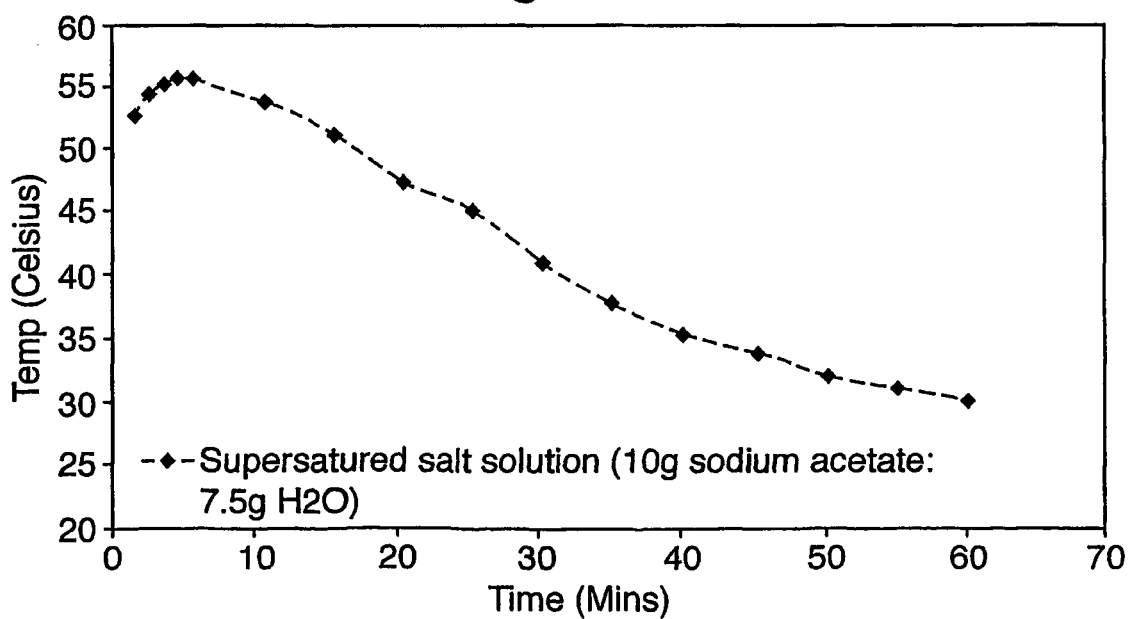
FIG. 13 is a graph representing the temperature changes noted for the formulation of Example 7.
Figure 14:
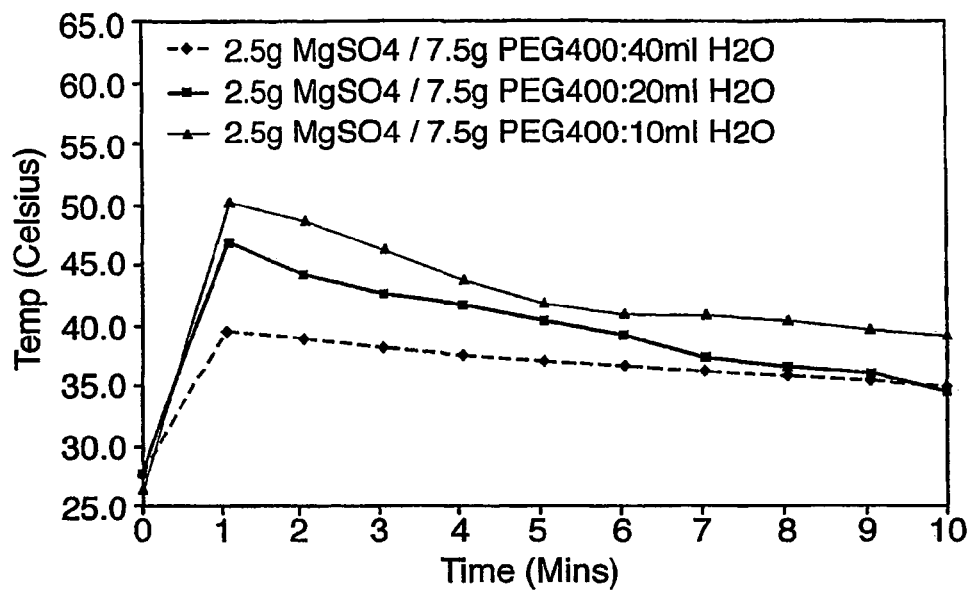
FIG. 14 is a graph representing the temperature changes noted for the formulations of Examples 8 to 10.
Figure 15:
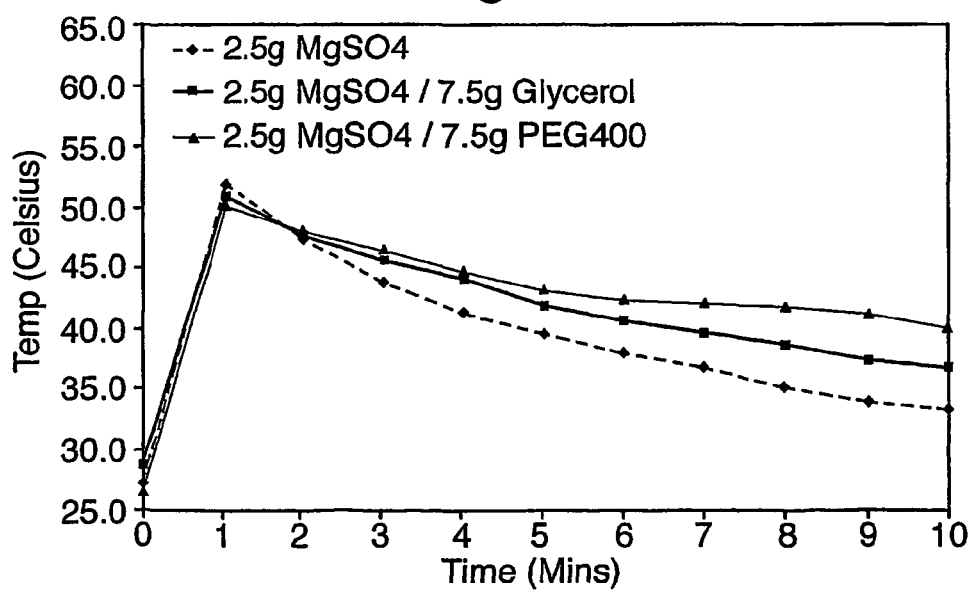
FIG. 15 is a graph representing the temperature changes noted for the formulations of Examples 11 to 13.
Figure 16:
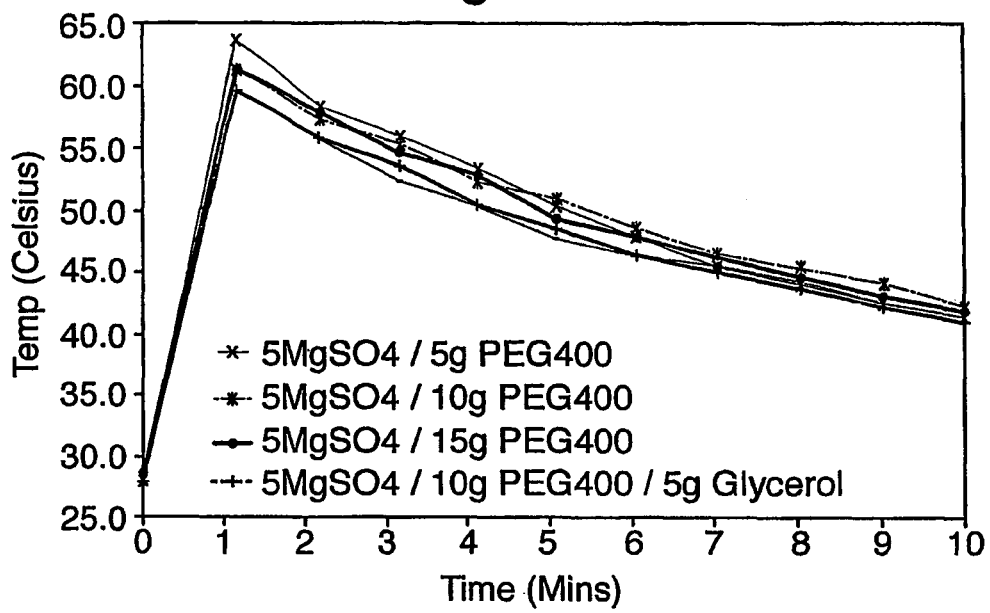
FIG. 16 is a graph representing the temperature changes noted for the formulations of Examples 14 to 17.
Figure 17:
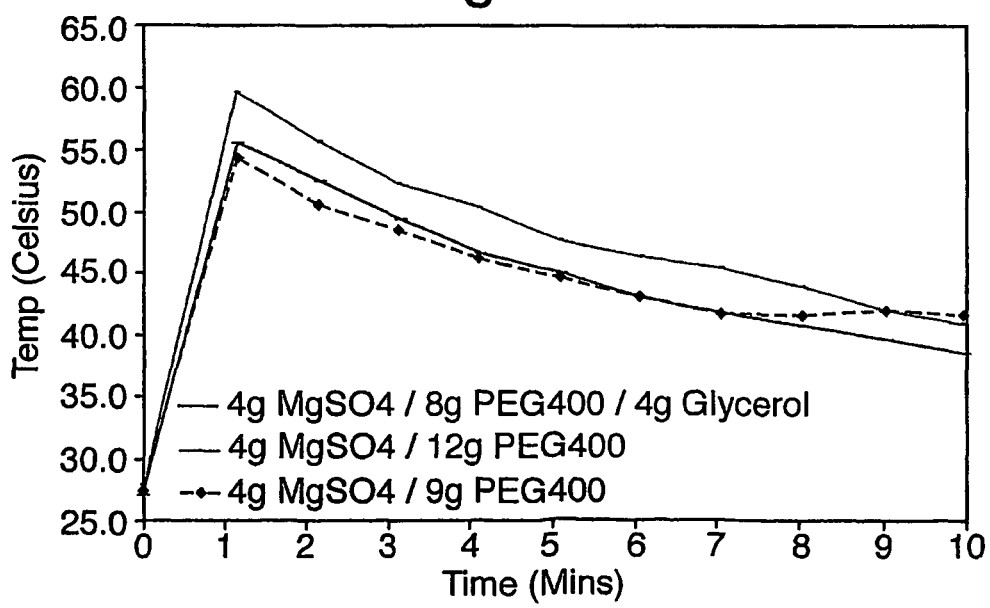
FIG. 17 is a graph representing the temperature changes noted for the formulations of Examples 18 to 20.
Figure 18:
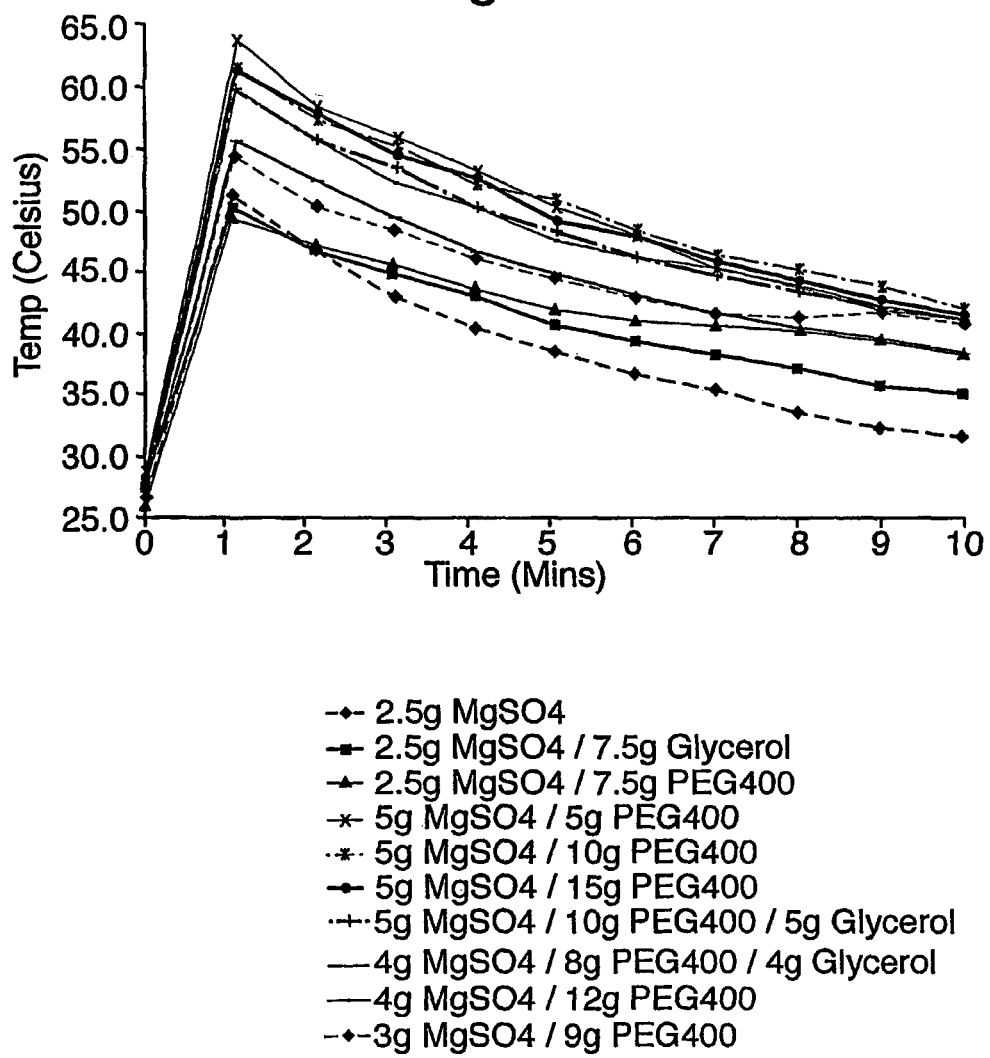
FIG. 18 is a graph representing the temperature changes noted for the formulations of Examples 21 to 30.
Figure 19:
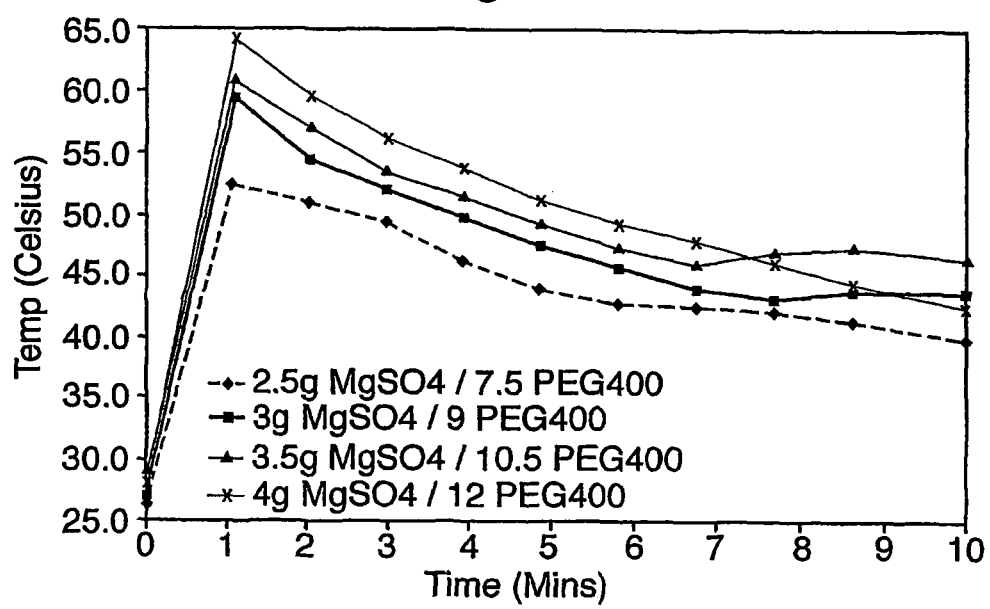
FIG. 19 is a graph representing the temperature changes noted for the formulations of Examples 31 to 34.

Two Component System B Utilising a Supersaturated Salt Solution 10 g anhydrous sodium acetate were mixed with 7.5 g water. After the addition of a few salt seed crystals, the temperature changes were measured and are represented in FIG. 13.

EXAMPLES 8 TO 30

Optimisation of Temperature Profile

In order to optimise the temperature profile for an inorganic salt/water system various compositions as detailed in Table 3 were investigated. The temperature changes measured are represented graphically in FIGS. 14 to 19.

TABLE 3

| Example | Formulation | FIG. |
|---|---|---|
| 8 | 2.5 g $MgSO_4$/7.5 g PEG 400:40 ml $H_2O$ | 14 |
| 9 | 2.5 g $MgSO_4$/7.5 g PEG 400:20 ml $H_2O$ | 14 |
| 10 | 2.5 g $MgSO_4$/7.5 g PEG 400:10 ml $H_2O$ | 14 |
| 11 | 2.5 g $MgSO_4$:10 ml $H_2O$ | 15 |
| 12 | 2.5 g $MgSO_4$/7.5 g glycerol:10 ml $H_2O$ | 15 |
| 13 | 2.5 g $MgSO_4$/7.5 g PEG 400:10 ml $H_2O$ | 15 |
| 14 | 5 g $MgSO_4$/5 g PEG 400:10 ml $H_2O$ | 16 |
| 15 | 5 g $MgSO_4$/10 g PEG 400:10 ml $H_2O$ | 16 |
| 16 | 5 g $MgSO_4$/15 g PEG 400:10 ml $H_2O$ | 16 |
| 17 | 5 g $MgSO_4$/10 g PEG 400/5 g glycerol:10 ml $H_2O$ | 16 |
| 18 | 4 g $MgSO_4$/8 g PEG 400/4 g glycerol:10 ml $H_2O$ | 17 |
| 19 | 4 g $MgSO_4$/12 g PEG 400:10 ml $H_2O$ | 17 |
| 20 | 3 g $MgSO_4$/9 g PEG 400:10 ml $H_2O$ | 17 |
| 21 | 2.5 g $MgSO_4$:10 ml $H_2O$ | 18 |
| 22 | 2.5 g $MgSO_4$/7.5 g glycerol:10 ml $H_2O$ | 18 |
| 23 | 2.5 g $MgSO_4$/7.5 g PEG 400:10 ml $H_2O$ | 18 |
| 24 | 5 g $MgSO_4$/5 g PEG 400:10 ml $H_2O$ | 18 |
| 25 | 5 g $MgSO_4$/10 g PEG 400:10 ml $H_2O$ | 18 |
| 26 | 5 g $MgSO_4$/15 g PEG 400:10 ml $H_2O$ | 18 |
| 27 | 5 g $MgSO_4$/10 g PEG 400/5 g glycerol:10 ml $H_2O$ | 18 |
| 28 | 4 g $MgSO_4$/8 g PEG 400/4 g glycerol:10 ml $H_2O$ | 18 |
| 29 | 4 g $MgSO_4$/12 g PEG 400:10 ml $H_2O$ | 18 |
| 30 | 3 g $MgSO_4$/9 g PEG 400:10 ml $H_2O$ | 18 |

For the formulations of Examples 23 and 30 the heat generated was better sustained between 7 and 10 minutes post activation and therefore offered advantages when compared with the other formulations.

EXAMPLES 31 TO 34

Further tests were carried out to optimise the salt mixture system with $MgSO_4$ from 2.5 g to 4 g. The details are set out in Table 4 and the temperature profile are represented graphically in FIG. 19.

TABLE 4

| Example | Formulation | FIG. |
|---|---|---|
| 31 | 2.5 g $MgSO_4$/7.5 g PEG 400:10 ml $H_2O$ | 19 |
| 32 | 3 g $MgSO_4$/9 g PEG 400:10 ml $H_2O$ | 19 |
| 33 | 3.5 g $MgSO_4$/10.5 g PEG 400:10 ml $H_2O$ | 19 |
| 34 | 4 g $MgSO_4$/12 g PEG 400:10 ml $H_2O$ | 19 |

The formulation of Example 33 sustained a temperature of just below 45° C. after 7 minutes and was therefore chosen for use in Example 35 in the production of a prototype wipe.

EXAMPLE 35

Prototype Heating Wipe

Figure 20:
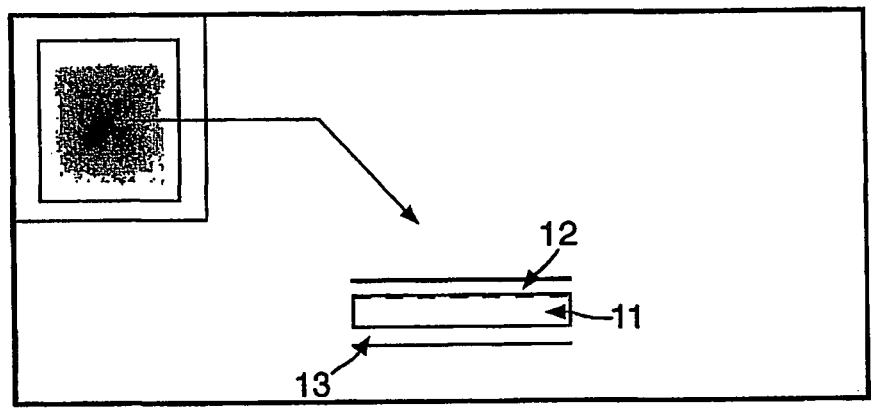
FIG. 20 is a schematic representation of the wipe of Example 35.
Figure 22:
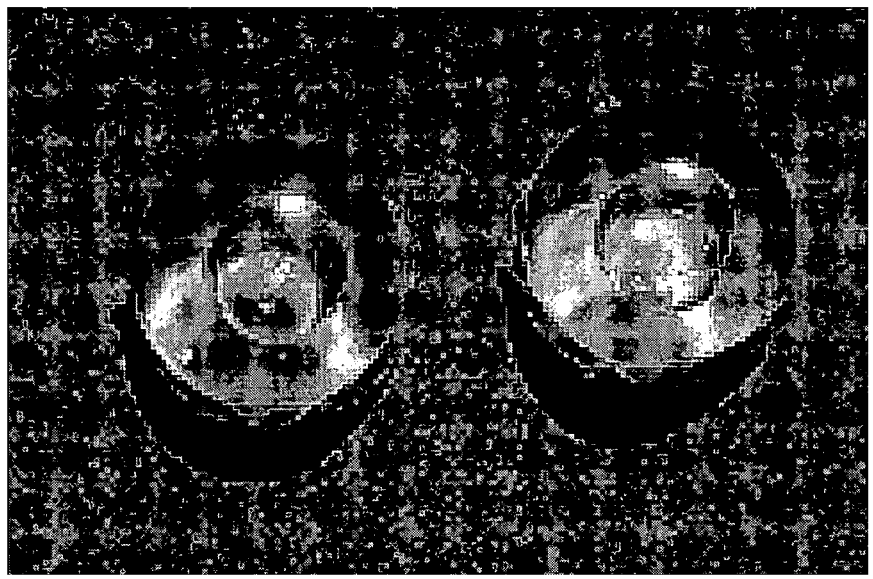
FIG. 22 is a picture of the water bubbles used in Example 35.
Figure 23:
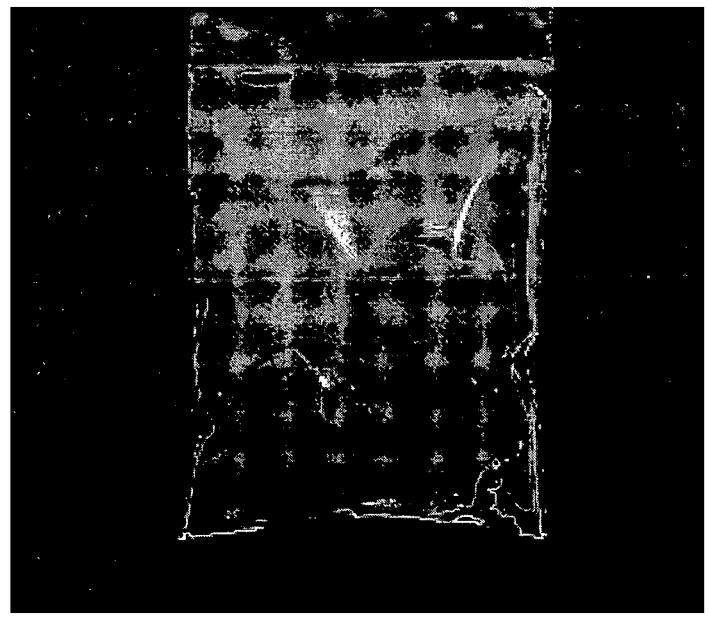
FIG. 23 is a picture of part of a prototype wipe of Example 35.

A prototype was produced based on a water triggered system which was activated by pressure. The heat produced was the result of the exothermic reaction of the inorganic salt mixture with water. The water was provided as a water bubble within a frangible plastic envelope of polyethylene as illustrated in FIG. 22. Two water bubbles were used each containing 5 ml water. The water bubbles and the salt mixture of 3.5 g $MgSO_4$/10.5 g PEG 400 were inserted in a sealable watertight pouch to form the heat-generating compartment 11 of FIG. 20. The heat generating compartment 11 is coated on one side 12 with a sheet of aluminium foil covered with gauze and on the other side 13 with a cotton pad. In use it is the side 12 which is applied to the closed eyelids for the heat treatment. After heat treatment side 13 can be impregnated with cleaning solution and used to wipe the lid margin. The pad on side 13 may, in an alternative arrangement, be pre-impregnated with the cleaning solution. A picture of the prototype wipe is in FIG. 23. In production the wipe will generally be of an optimum size and shape for use by the user.

Figure 21:
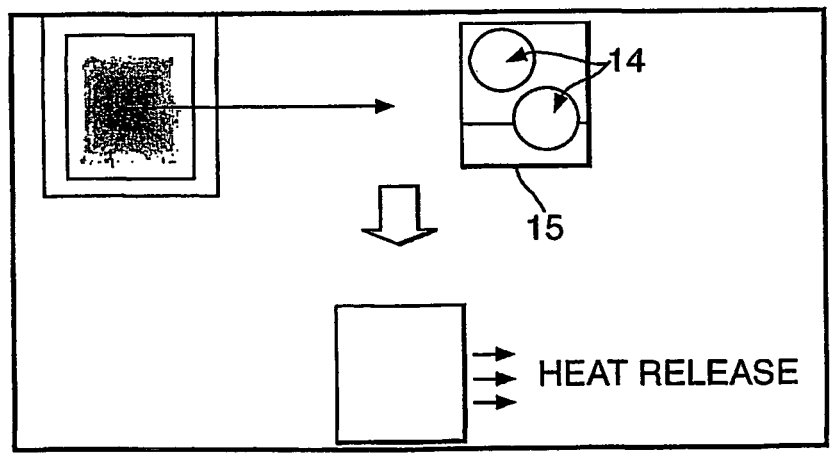
FIG. 21 is a further schematic representation of the wipe of Example 35 at activation.
Figure 24:
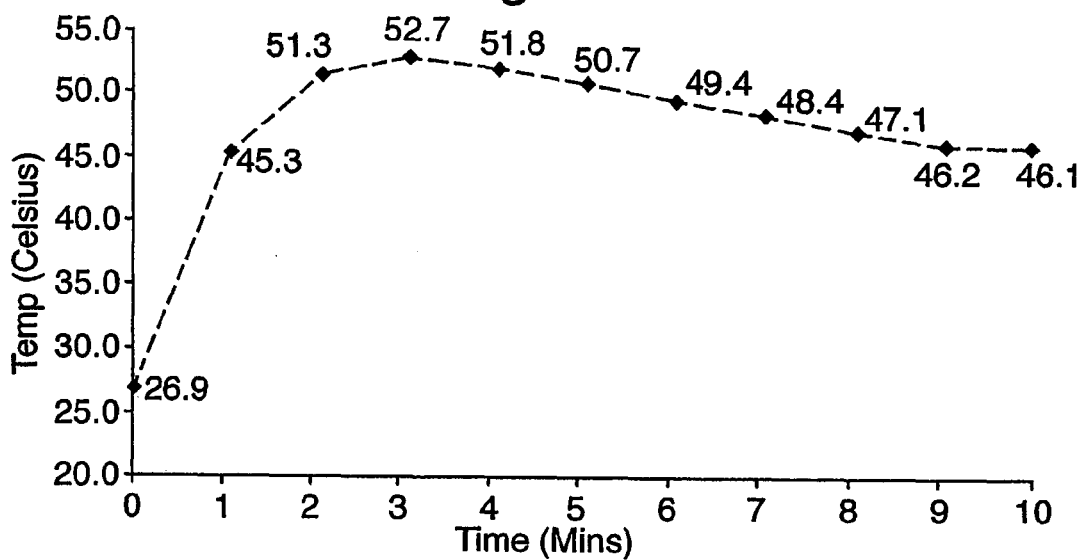
FIG. 24 is a graph of the temperature profile achieved for the wipe of Example 35.
Figure 26:
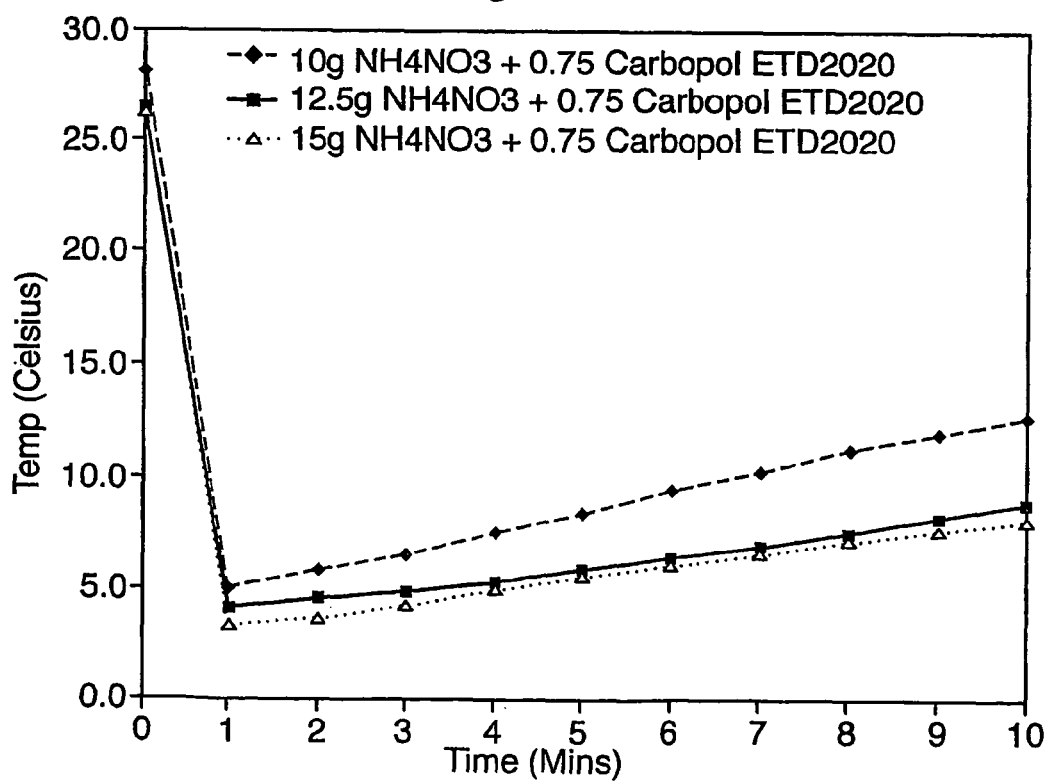
FIG. 26 is a graph representing the temperature changes noted for the formulations of Examples 47 to 49.

The operation of wipe is illustrated schematically in FIG. 21. Gentle pressure on the external surfaces of the wipe causes the water bubbles 14 to burst so that the water comes into contact with the inorganic salt mixture 15 so that heat is released. The temperature profile is illustrated graphically in FIG. 24. As indicated above, a temperature of from 45 to 52° C. is desirable. The wipe reached the required temperature within 1 minute of activation and the temperature was maintained for 10 minutes. Crystallisation occurred.

EXAMPLE 36 to 46

Water Triggered System for Cooling

Figure 25:
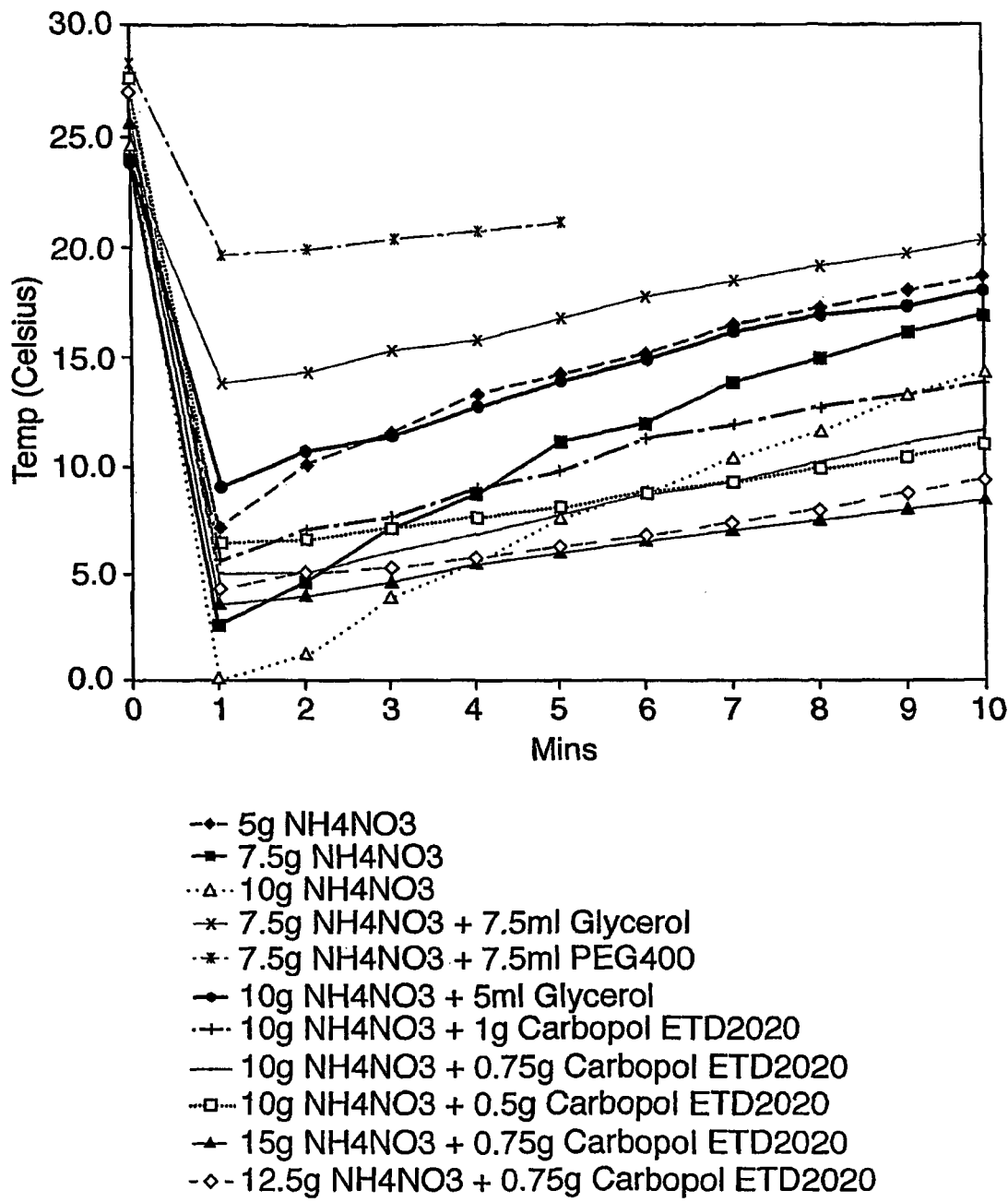
FIG. 25 is a graph representing the temperature changes noted for the formulations of Examples 36 to 46.
Figure 27:
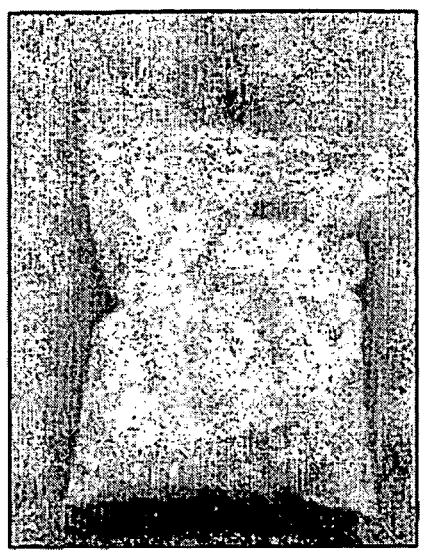
FIG. 27 is a picture of uncoated cooling prototype.

Various compositions were prepared as detailed in Table 5 and the temperature profiles on the addition of water were measured. The results are illustrated graphically in FIG. 25.

TABLE 5

| Example | Formulation | FIG. |
|---|---|---|
| 36 | 5 g $NH_4NO_3$:10 ml $H_2O$ | 25 |
| 37 | 7.5 g $NH_4NO_3$:10 ml $H_2O$ | 25 |
| 38 | 10 g $NH_4NO_3$:10 ml $H_2O$ | 25 |
| 39 | 7.5 g $NH_4NO_3$/7.5 ml glycerol:10 ml $H_2O$ | 25 |
| 40 | 7.5 g $NH_4NO_3$/7.5 ml PEG400:10 ml $H_2O$ | 25 |
| 41 | 10 g $NH_4NO_3$/5 ml glycerol:10 ml $H_2O$ | 25 |
| 42 | 10 g $NH_4NO_3$/1 g Carbopol ETD2020:10 ml $H_2O$ | 25 |
| 43 | 10 g $NH_4NO_3$/0.75 g Carbopol ETD2020:10 ml $H_2O$ | 25 |
| 44 | 10 g $NH_4NO_3$/0.5 g Carbopol ETD2020:10 ml $H_2O$ | 25 |
| 45 | 15 g $NH_4NO_3$/0.75 g Carbopol ETD2020:10 ml $H_2O$ | 25 |
| 46 | 12.5 g $NH_4NO_3$/0.75 g Carbopol ETD2020:10 ml $H_2O$ | 25 |
| 47 | 10 g $NH_4NO_3$/0.75 g Carbopol ETD2020:10 ml $H_2O$ | 26 |
| 48 | 12.5 g $NH_4NO_3$/0.75 g Carbopol ETD2020:10 ml $H_2O$ | 26 |
| 49 | 15 g $NH_4NO_3$/0.75 g Carbopol ETD2020:10 ml $H_2O$ | 26 |

EXAMPLE 50

Prototype Cooling Wipe

Figure 28:
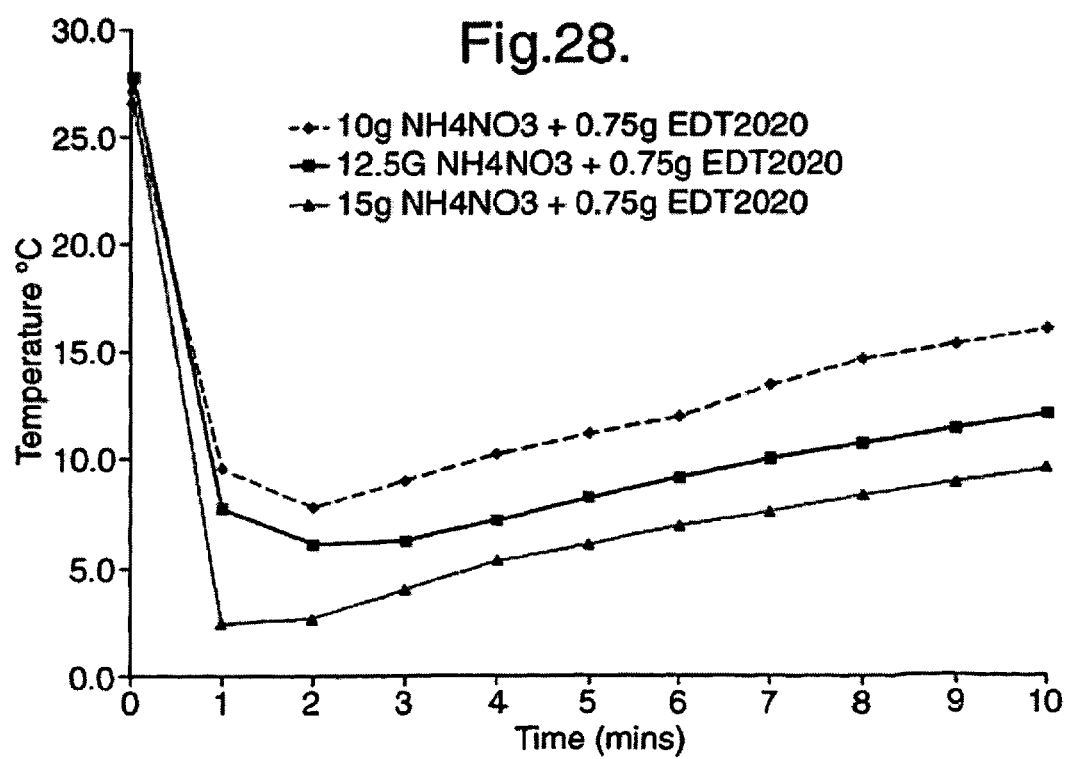
FIG. 28 is a graph representing the temperature changes noted for the formulations of Example 50.

A prototype was produced based on a water triggered system which was activated by pressure. The cold produced was the result of the endothermic reaction of the ammonium nitrate with water. The water was provided as a water bubble within a frangible plastic envelope of polyethylene as illustrated in FIG. 22. One water bubble was used containing 10 ml water. The water bubble and the salt mixture of 10 g to 15 g $NH_4NO_3$/0.75 g ETD2020 (detailed in Table 6) were inserted in a sealable water-tight pouch to form the cold-generating compartment 21 of FIG. 29. In this example, the cold generating compartment 21 was left uncoated. Pressure was applied to the water bubble such that the water mixed with the ammonium nitrate and cold was generated. The temperature profiles are illustrated graphically in FIG. 28.

TABLE 6

| Run | Formulation | FIG. |
|---|---|---|
| A | 10 g $NH_4NO_3$/0.75 g ETD2020:10 ml $H_2O$ | 28 |
| B | 12.5 g $NH_4NO_3$/0.75 g ETD2020:10 ml $H_2O$ | 28 |
| C | 15 g $NH_4NO_3$/0.75 g ETD2020:10 ml $H_2O$ | 28 |

EXAMPLE 51

Prototype Cooling Wipe 2

Figure 31:
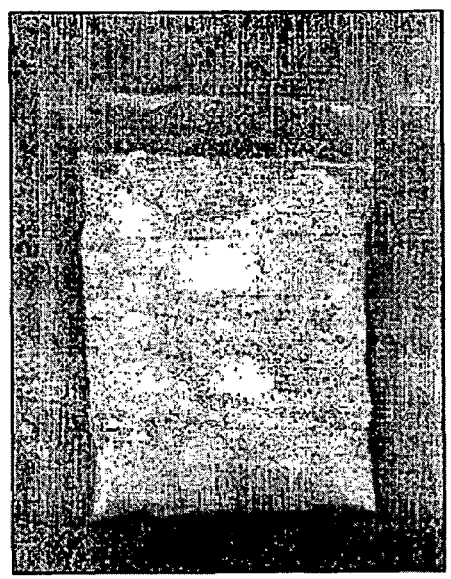
FIG. 31 is a picture of an alternative cooling prototype.

Example 51 was repeated except that the wipe was left uncoated on one side 22 and was coated on the other side 23 with a cotton pad. In use it is the side 22 which is to be applied to the closed eyelids for the cooling treatment. After cooling treatment side 23 can be impregnated with any applicable treatment solution and used to wipe the lid margin. The pad on side 23 may be pre-impregnated with the cleaning solution. A picture of the prototype wipe is in FIG. 31. In production the wipe will generally be of an optimum size and shape for use by the user.

Figure 32:
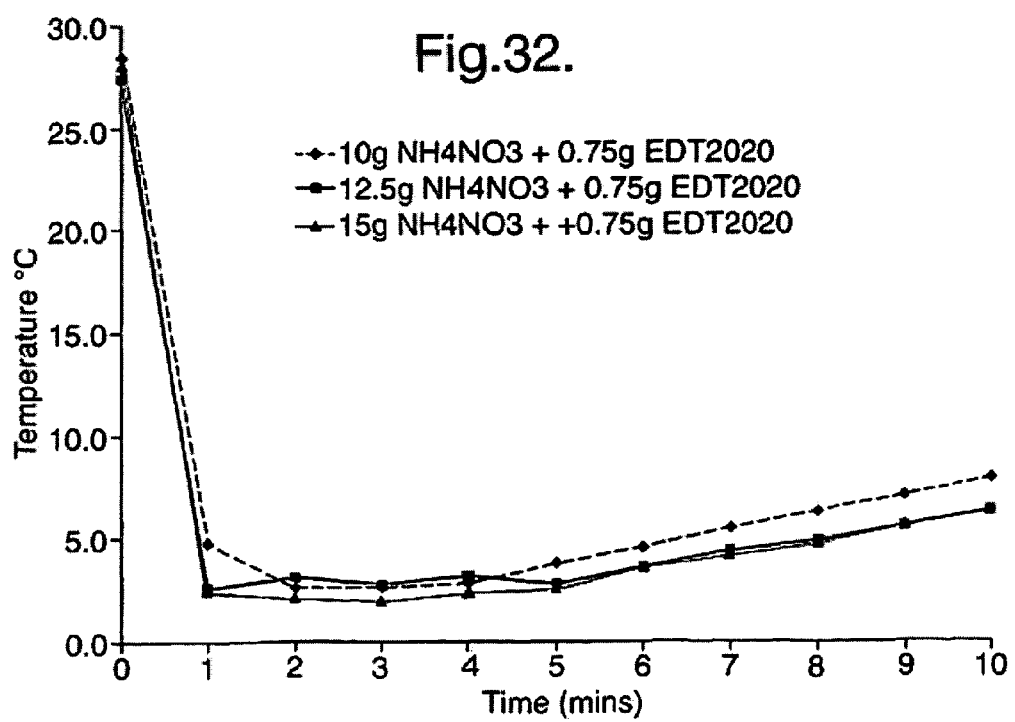
FIG. 32 is a graph representing the temperature changes noted for the formulations of Example 51.

The operation of the wipe is illustrated schematically in FIG. 30. Gentle pressure on the external surfaces of the wipe causes the water bubble 24 to burst so that the water comes into contact with the inorganic salt mixture 25 so that cooling is released. The temperature profile is illustrated graphically in FIG. 32.

EXAMPLE 52

Prototype Finger Shaped Heating Wipe

Figure 33:
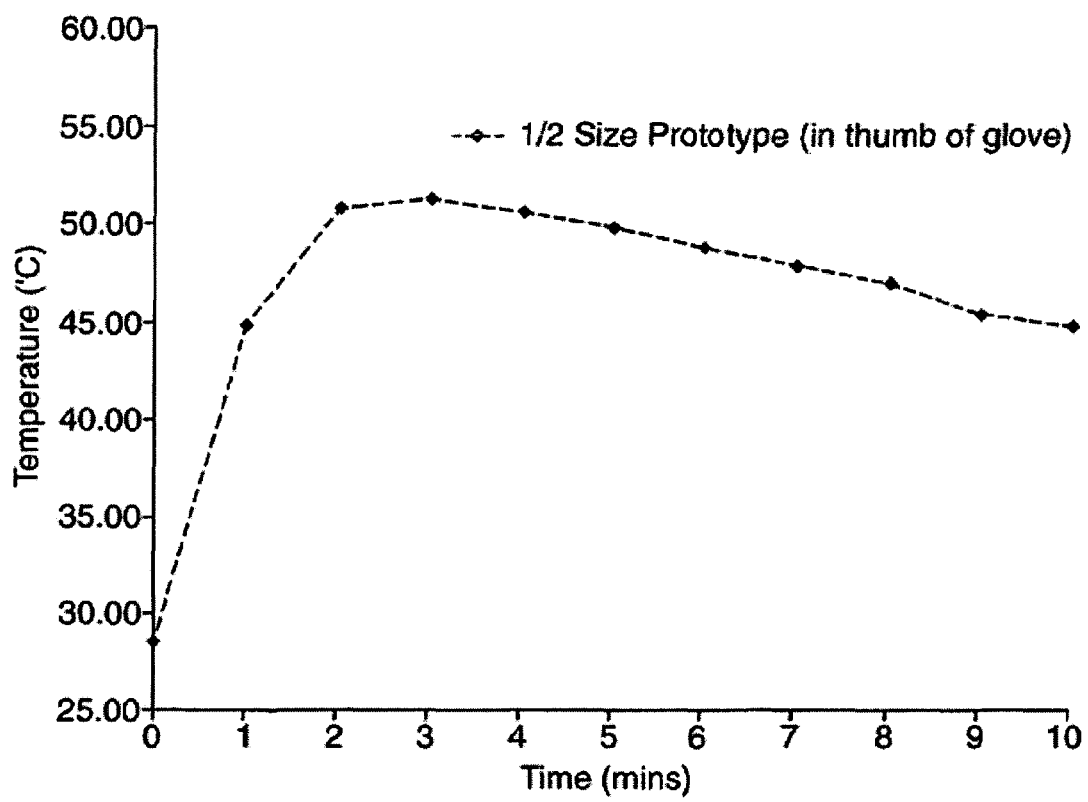
FIG. 33 is a graph representing the temperature changes noted for the finger shaped arrangement of Example 52.

Example 35 was repeated except that the water bubbles and the salt mixture in the sealable water-tight pouch were placed in the thumb of a glove. The temperature profile achieved is illustrated graphically in FIG. 33.

EXAMPLE 53

Alternative Prototype

Two plastics sheets comprising three layers, an outer layer of polypropylene, an amorphous intermediate metallic oxide layer and an inner layer of polyethylene, are thermo-sealed around three sides to form a pouch. The pouch is then further sealed with a rupturable seal in the middle to create two chambers. A salt/PEG mixture is placed in one chamber and water into the other. The mouth of the pouch is then thermo-sealed. One external face of the pouch is coated with a polystyrene insulating layer and gauze is applied to the other face which when the wipe is in use will be in contact with the eyelid margin.

What is claimed is:

1. An eyelid margin wipe for treatment of disorders of an eyelid or eyelid margin comprising: at least two components adapted to change a temperature of the wipe from an ambient temperature upon reaction with each other to an elevated temperature range of from about 40° C. to about 55° C.; a water-impermeable container that prevents the at least two components from coming into contact with a closed eye when in use; a seal for keeping the at least two components separate until temperature change is initiated, wherein the elevated temperature range is reached within 2 minutes after the temperature change is initiated and is maintained for at least 5 minutes without causing damage to a delicate eye region; and at least one agent selected from the group consisting of cleansing agents and surfactant agents, wherein the wipe has a size of one human eye region.

2. The eyelid margin wipe according to claim 1, wherein the disorder of the eyelid margin is meibomian gland dysfunction.

3. The eyelid margin wipe according to claim 1, wherein the wipe is sterile.

4. The eyelid margin wipe according to claim 1, wherein the reaction is an exothermic reaction.

5. The eyelid margin wipe according to claim 1, wherein the at least two components comprise $MgSO_4$ and water.

6. The eyelid margin wipe according to claim 1, wherein the at least two components comprise an inorganic salt and water.

7. The eyelid margin wipe according to claim 1, wherein the at least two components comprise an oxidising agent and a reducing agent.

8. The eyelid margin wipe according to claim 1, wherein the temperature is changed to a temperature of from about 40° C. to about 45° C.

9. The eyelid margin wipe according to claim 1, wherein the temperature is changed to a temperature of from about 45° C. to about 52° C.

10. The eyelid margin wipe according to claim 1, wherein the elevated temperature is reached within 1 minute.

11. The eyelid margin wipe according to claim 1, wherein the temperature is maintained at the elevated temperature range for more than 5 minutes.

12. The eyelid margin wipe according to claim 1, wherein the temperature is maintained at the elevated temperature range for 10 minutes or more.

13. The eyelid margin wipe according to claim 1, wherein the wipe is square, rectangular, circular or ovoid shaped.

14. The eyelid margin wipe according to claim 1, wherein the wipe is eye-shaped.

15. The eyelid margin wipe according to claim 1, wherein the wipe is curved to correspond to a contour of an eye.

16. The eyelid margin wipe according to claim 1, wherein the wipe is coated with a polymeric material capable of moulding to a surface of the eye.

17. The eyelid margin wipe according to claim 1, wherein the wipe is coated with a polymeric material which softens at a temperature above ambient temperature, such that, in use, the polymeric material is capable of moulding to the surface of the eye.

18. The eyelid margin wipe according to claim 1, further comprising at least one active agent.

19. The eyelid margin wipe according to claim 1, further comprising a drug delivery system.

20. The eyelid margin wipe according to claim 1, further comprising at least one additional agent selected from the group consisting of antistatic agents, preservatives, antioxidants, antimicrobial agents, chelating agents, emollients, emulsifying agents, buffering/neutralising agents, humectants, thickeners, viscosity controlling agents, antistatic agents, and conditioning agents.

21. The eyelid margin wipe according to claim 20, wherein the at least one additional agent is incorporated in a thermo-responsive polymer layer coated on a surface of the wipe.

22. The eyelid margin wipe according to claim 20, wherein the viscosity controlling agent is polyethylene glycol (PEG).

23. The eyelid margin wipe according to claim 20, further comprising a reflective layer and/or a conductive layer to direct heat towards one surface of the wipe.

24. The eyelid margin wipe according to claim 1, wherein the at least one agent is comprising a cleansing agent.

25. The eyelid margin wipe according to claim 1, wherein the at least one agent is a surfactant agent.

26. The eyelid margin wipe according to claim 1, wherein at least one of the cleansing agent and the surfactant agent is selected from the group consisting of PEG-80 sorbitan laurate, sodium trideceth sulfate, PEG-150 distearate, cocamidopropyl hydroxysultaine, sodium laureth-13 carboxylate, disodium lauroamphodiacetate, polysorbate 80, polysorbate 20, poloxamer 184, ammonium laureth sulfate, ceteareth 20, ceteareth 25, cocamidopropyl betaine, disodium laureth sulfosuccinate, disodium lauriminodipropionate, disodium lauroamphodipropionate, glycol stearate, hydrogenated castor oil, laureth-23, magnesium laureth, oleth sulfate, PEG-20 stearate, PEG-35 castor oil, PEG-40 hydrogenated castor oil, PEG-60 hydrogenated castor oil, PEG-7 hydrogenated castor oil, PEG-75 lanolin, poloxamer, sodium laureth sulfate, sodium trideceth sulfate, sodium C12-15 pareth 15 sulfonate, and sodium C14-16 olefin sulfonate.

27. The eyelid margin wipe according to claim 1, further comprising an indicator which confirms to a user that a required temperature has been reached.

28. The eyelid margin wipe according to claim 27, wherein the indicator is a temperature sensitive color indicator configured to change from a first color to a second color when the required temperature has been reached.

29. The eyelid margin wipe according to claim 28, wherein the indicator is configured to undergo a reversible color change, such that when the wipe is no longer at the required temperature or has fallen outside of a required temperature range, the indicator is configured to revert to the first color.

30. The eyelid margin wipe according to claim 28, wherein at least a part of the wipe is coated with an indicator selected from the group consisting of a temperature reactive ink and a temperature reactive dye.

31. The eyelid margin wipe according to claim 1, wherein the seal is a frangible seal.

* * * * *

UNITED STATES PATENT AND TRADEMARK OFFICE
CERTIFICATE OF CORRECTION

PATENT NO. : 8,506,539 B2  
APPLICATION NO. : 11/120757  
DATED : August 13, 2013  
INVENTOR(S) : Michel Guillon et al.

Page 1 of 1

It is certified that error appears in the above-identified patent and that said Letters Patent is hereby corrected as shown below:

In the Claims

Column 21, Lines 18 and 19:

In Claim 24: "The eyelid margin wipe according to claim 1, wherein the at least one agent is comprising a cleansing agent." should be --The eyelid margin wipe according to claim 1, wherein the at least one agent is a cleansing agent.--.

Signed and Sealed this  
Eleventh Day of March, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,506,539 B2  Page 1 of 1
APPLICATION NO. : 11/120757
DATED : August 13, 2013
INVENTOR(S) : Michel Guillon et al.

It is certified that error appears in the above-identified patent and that said Letters Patent is hereby corrected as shown below:

In the Claims

COLUMN 20, LINES 32-34:

In Claim 6 "The eyelid margin wipe according to claim 1, wherein the at least two components comprise an inorganic salt and water." should be --The eyelid margin wipe according to claim 1, wherein one of the at least two components is a hydratable inorganic salt.--.

Signed and Sealed this
Fifteenth Day of April, 2014

Michelle K. Lee
*Deputy Director of the United States Patent and Trademark Office*